(12) United States Patent
Somamoto et al.

(10) Patent No.: US 11,969,512 B2
(45) Date of Patent: Apr. 30, 2024

(54) METHOD FOR PRODUCING PROTEIN COMPOSITION, AND PROTEIN COMPOSITION

(71) Applicant: SANYO CHEMICAL INDUSTRIES, LTD., Kyoto (JP)

(72) Inventors: Satoshi Somamoto, Kyoto (JP); Shingo Kawabata, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 246 days.

(21) Appl. No.: 17/336,672

(22) Filed: Jun. 2, 2021

(65) Prior Publication Data

US 2021/0290790 A1 Sep. 23, 2021

Related U.S. Application Data

(62) Division of application No. 15/556,765, filed as application No. PCT/JP2016/057430 on Mar. 9, 2016, now abandoned.

(30) Foreign Application Priority Data

Mar. 12, 2015 (JP) ................................. 2015-049302

(51) Int. Cl.
| | | |
|---|---|---|
| A61L 2/08 | (2006.01) | |
| C07K 1/00 | (2006.01) | |
| C07K 1/06 | (2006.01) | |
| C07K 1/26 | (2006.01) | |
| C07K 14/78 | (2006.01) | |

(52) U.S. Cl.
CPC .................. *A61L 2/08* (2013.01); *C07K 1/00* (2013.01); *C07K 1/061* (2013.01); *C07K 1/26* (2013.01); *A61L 2202/20* (2013.01); *C07K 14/78* (2013.01)

(58) Field of Classification Search
None
See application file for complete search history.

(56) References Cited

U.S. PATENT DOCUMENTS

| | | | |
|---|---|---|---|
| 2002/0045567 A1* | 4/2002 | Cappello | A61L 27/227 |
| | | | 530/331 |
| 2003/0059338 A1 | 3/2003 | Mann et al. | |
| 2010/0029542 A1 | 2/2010 | Jezek | |
| 2014/0194370 A1* | 7/2014 | Cappello | C07K 14/78 |
| | | | 530/353 |

FOREIGN PATENT DOCUMENTS

| | | |
|---|---|---|
| JP | 2000-514778 | 11/2000 |
| JP | 2003-527210 | 9/2003 |
| JP | 2010-514747 | 5/2010 |
| JP | 2012-521776 | 9/2012 |
| WO | 97/17435 | 5/1997 |
| WO | 01/70279 | 9/2001 |
| WO | 02/103029 | 12/2002 |
| WO | 03/026704 | 4/2003 |
| WO | 2008/081166 | 7/2008 |
| WO | 2010/112576 | 10/2010 |
| WO | 2016/196662 | 12/2016 |
| WO | WO-2016196662 A1 * | 12/2016 ............. A61L 2/087 |

OTHER PUBLICATIONS

Johnson B and Moser K "Amino Acid Destruction in Beer by High Energy Electron Beam Irradiation" Radiation Preservation of Food , Advances in Chemistry, ACS. (Year: 1967).*
Choe E and Min D "Mechanisms of Antioxidants in the Oxidation of Foods" Comprehensive Reviews in Food Science and Food Safety 8:345-358. (Year: 2009).*
Anonymous "Hydrogen Bonds" Proteopedia http://www.proteopedia.org/wiki/index.php/Hydrogen_Bonds (Year: 2013).*
Zhao et al., "Update Application and Development of Radiation Sterilization Technology on Pharmaceutical Industry", Journal of Nuclear Agricultural Sciences, 2006, vol. 20, No. 2, pp. 143-147.
Domazou et al., "Repair of Protein Radicals by Antioxidants", Review, Israel Journal of Chemistry, 2014, vol. 54, pp. 254-264, 11 pages.
Zbikowska et al., "Protein modification caused by a high dose of gamma irradiation in cryo-sterilized plasma: Protective effects of ascorbate", Free Radical Biology & Medicine, 2006, vol. 40, pp. 536-542.
Johnson and Moser "Amino Acid Destruction in Beef by High Energy Electron Beam Irradiation" Radiation Preservation of Foods, Advances in Chemistry, American Chemical Society, Washington DC (Year: 1967).
Choe and Min "Mechanisms of Antioxidants in the Oxidation of Foods" Comprehensive Reviews in Food Science and Food Safety, 8:345-358 (Year: 2009).

(Continued)

*Primary Examiner* — Sudhakar Katakam
*Assistant Examiner* — Zachary J Miknis
(74) *Attorney, Agent, or Firm* — Wenderoth, Lind & Ponack, L.L.P.

(57) ABSTRACT

A method for producing a protein composition containing a protein (A), a radical scavenger (RS), and at least one hydrogen-bond-formable compound (HC) selected from the group consisting of amino acids, peptides, and proteins other than the protein (A). The method including a sterilization step of radiosterilizing an unsterilized protein composition, wherein the unsterilized protein composition contains the protein (A), the radical scavenger (RS), and the hydrogen-bond-formable compound (HC), the protein (A) contains at least one functional group selected from the group consisting of sulfide, amide, hydroxyl, amino, and carboxyl groups, the hydrogen-bond-formable compound (HC) contains at least one functional group selected from the group consisting of sulfide, amide, hydroxyl, amino, and carboxyl groups, the at least one functional group in the protein (A) is capable of binding to the at least one functional group in the hydrogen-bond-formable compound (HC) via a hydrogen bond.

6 Claims, No Drawings

Specification includes a Sequence Listing.

(56) References Cited

OTHER PUBLICATIONS

Steinhart et al., "Pro- and Antioxidative Effect of Ascorbic Acid in L-Trypotphan in the System $Fe^{3+}$/Ascorbic Acid/$O_2$", J. Agric. Food Chem., 41:2275-2277 (Year: 1993).
International Search Report issued Jun. 7, 2016 in International Application No. PCT/JP2016/057430.

\* cited by examiner

SEQUENCE LISTING

```
<160> NUMBER OF SEQ ID NOS: 35

<210> SEQ ID NO 1
<211> LENGTH: 6
<212> TYPE: PRT
<213> ORGANISM: Bombyx mori

<400> SEQUENCE: 1

Gly Ala Gly Ala Gly Ser
1               5

<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5

<210> SEQ ID NO 3
<211> LENGTH: 5
<212> TYPE: PRT
<213> ORGANISM: Homo sapiens

<400> SEQUENCE: 3

Gly Val Gly Val Pro
1               5

<210> SEQ ID NO 4
<211> LENGTH: 5
<212> TYPE: PRT
<213> ORGANISM: Homo sapiens

<400> SEQUENCE: 4

Pro Gly Val Gly Val
1               5

<210> SEQ ID NO 5
<211> LENGTH: 5
<212> TYPE: PRT
<213> ORGANISM: Homo sapiens

<400> SEQUENCE: 5

Val Pro Gly Val Gly
1               5

<210> SEQ ID NO 6
<211> LENGTH: 5
<212> TYPE: PRT
<213> ORGANISM: Homo sapiens
```

```
<400> SEQUENCE: 6

Gly Val Pro Gly Val
1               5

<210> SEQ ID NO 7
<211> LENGTH: 5
<212> TYPE: PRT
<213> ORGANISM: Homo sapiens

<400> SEQUENCE: 7

Val Gly Val Pro Gly
1               5

<210> SEQ ID NO 8
<211> LENGTH: 9
<212> TYPE: PRT
<213> ORGANISM: Homo sapiens

<400> SEQUENCE: 8

Gly Ala His Gly Pro Ala Gly Pro Lys
1               5

<210> SEQ ID NO 9
<211> LENGTH: 5
<212> TYPE: PRT
<213> ORGANISM: Bombyx mori

<400> SEQUENCE: 9

Val Ala Ala Gly Tyr
1               5

<210> SEQ ID NO 10
<211> LENGTH: 7
<212> TYPE: PRT
<213> ORGANISM: Bombyx mori

<400> SEQUENCE: 10

Gly Ala Gly Ala Gly Ala Ser
1               5

<210> SEQ ID NO 11
<211> LENGTH: 6
<212> TYPE: PRT
<213> ORGANISM: Homo sapiens

<400> SEQUENCE: 11

Leu Gly Pro Leu Gly Pro
1               5

<210> SEQ ID NO 12
<211> LENGTH: 9
<212> TYPE: PRT
<213> ORGANISM: Homo sapiens

<400> SEQUENCE: 12

Gly Ala His Gly Pro Ala Gly Pro Lys
1               5

<210> SEQ ID NO 13
<211> LENGTH: 18
<212> TYPE: PRT
<213> ORGANISM: Homo sapiens
```

```
<400> SEQUENCE: 13

Gly Ala Pro Gly Pro Ala Gly Pro Pro Gly Ser Arg Gly Asp Pro Gly
1               5                   10                  15

Pro Pro

<210> SEQ ID NO 14
<211> LENGTH: 9
<212> TYPE: PRT
<213> ORGANISM: Homo sapiens

<400> SEQUENCE: 14

Gly Ala Gln Gly Pro Ala Gly Pro Gly
1               5

<210> SEQ ID NO 15
<211> LENGTH: 15
<212> TYPE: PRT
<213> ORGANISM: Homo sapiens

<400> SEQUENCE: 15

Gly Ala Pro Gly Ala Pro Gly Ser Gln Gly Ala Pro Gly Leu Gln
1               5                   10                  15

<210> SEQ ID NO 16
<211> LENGTH: 15
<212> TYPE: PRT
<213> ORGANISM: Homo sapiens

<400> SEQUENCE: 16

Gly Ala Pro Gly Thr Pro Gly Pro Gln Gly Leu Pro Gly Ser Pro
1               5                   10                  15

<210> SEQ ID NO 17
<211> LENGTH: 17
<212> TYPE: PRT
<213> ORGANISM: Homo sapiens

<400> SEQUENCE: 17

Gly Ala Ala Val Thr Gly Arg Gly Asp Ser Pro Ala Ser Ala Ala Gly
1               5                   10                  15

Tyr

<210> SEQ ID NO 18
<211> LENGTH: 20
<212> TYPE: PRT
<213> ORGANISM: Homo sapiens

<400> SEQUENCE: 18

Gly Ala Ala Pro Gly Ala Ser Ile Lys Val Ala Val Ser Ala Gly Pro
1               5                   10                  15

Ser Ala Gly Tyr
            20

<210> SEQ ID NO 19
<211> LENGTH: 24
<212> TYPE: PRT
<213> ORGANISM: Artificial Sequence
<220> FEATURE:
<223> OTHER INFORMATION: Repeat sequence

<400> SEQUENCE: 19

Gly Ala Gly Ala Gly Ser Gly Ala Gly Ala Gly Ser Gly Ala Gly Ala
1               5                   10                  15
```

Gly Ser Gly Ala Gly Ala Gly Ser
            20

<210> SEQ ID NO 20
<211> LENGTH: 40
<212> TYPE: PRT
<213> ORGANISM: Artificial Sequence
<220> FEATURE:
<223> OTHER INFORMATION: Repeat sequence

<400> SEQUENCE: 20

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro
        35                  40

<210> SEQ ID NO 21
<211> LENGTH: 12
<212> TYPE: PRT
<213> ORGANISM: Artificial Sequence
<220> FEATURE:
<223> OTHER INFORMATION: Repeat sequence

<400> SEQUENCE: 21

Gly Ala Gly Ala Gly Ser Gly Ala Gly Ala Gly Ser
1               5                   10

<210> SEQ ID NO 22
<211> LENGTH: 874
<212> TYPE: PRT
<213> ORGANISM: Artificial Sequence
<220> FEATURE:
<223> OTHER INFORMATION: SELP8K

<400> SEQUENCE: 22

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
    130                 135                 140

Ala Gly Ala Gly Ser Gly Ala Gly Ala Gly Ser Gly Ala Gly Ala Gly
145                 150                 155                 160

Ser Gly Val Gly Val Pro Gly Val Gly Val Pro Gly Val Gly Val Pro
                165                 170                 175

-continued

```
Gly Val Gly Val Pro Gly Lys Gly Val Pro Gly Val Gly Val Pro Gly
            180                 185                 190
Val Gly Val Pro Gly Val Gly Val Pro Gly Ala Gly Ala Gly Ser Gly
            195                 200                 205
Ala Gly Ala Gly Ser Gly Ala Gly Ser Gly Ala Gly Ala Gly
            210                 215                 220
Ser Gly Val Gly Val Pro Gly Val Gly Val Pro Gly Val Gly Val Pro
225                 230                 235                 240
Gly Val Gly Val Pro Gly Lys Gly Val Pro Gly Val Gly Val Pro Gly
            245                 250                 255
Val Gly Val Pro Gly Val Gly Val Pro Gly Ala Gly Ala Gly Ser Gly
            260                 265                 270
Ala Gly Ala Gly Ser Gly Ala Gly Ala Gly Ser Gly Ala Gly Ala Gly
            275                 280                 285
Ser Gly Val Gly Val Pro Gly Val Gly Val Pro Gly Val Gly Val Pro
            290                 295                 300
Gly Val Gly Val Pro Gly Lys Gly Val Pro Gly Val Gly Val Pro Gly
305                 310                 315                 320
Val Gly Val Pro Gly Val Gly Val Pro Gly Ala Gly Ala Gly Ser Gly
            325                 330                 335
Ala Gly Ala Gly Ser Gly Ala Gly Ala Gly Ser Gly Ala Gly Ala Gly
            340                 345                 350
Ser Gly Val Gly Val Pro Gly Val Gly Val Pro Gly Val Gly Val Pro
            355                 360                 365
Gly Val Gly Val Pro Gly Lys Gly Val Pro Gly Val Gly Val Pro Gly
            370                 375                 380
Val Gly Val Pro Gly Val Gly Val Pro Gly Ala Gly Ala Gly Ser Gly
385                 390                 395                 400
Ala Gly Ala Gly Ser Gly Ala Gly Ala Gly Ser Gly Ala Gly Ala Gly
            405                 410                 415
Ser Gly Val Gly Val Pro Gly Val Gly Val Pro Gly Val Gly Val Pro
            420                 425                 430
Gly Val Gly Val Pro Gly Lys Gly Val Pro Gly Val Gly Val Pro Gly
            435                 440                 445
Val Gly Val Pro Gly Val Gly Val Pro Gly Ala Gly Ala Gly Ser Gly
            450                 455                 460
Ala Gly Ala Gly Ser Gly Ala Gly Ala Gly Ser Gly Ala Gly Ala Gly
465                 470                 475                 480
Ser Gly Val Gly Val Pro Gly Val Gly Val Pro Gly Val Gly Val Pro
            485                 490                 495
Gly Val Gly Val Pro Gly Lys Gly Val Pro Gly Val Gly Val Pro Gly
            500                 505                 510
Val Gly Val Pro Gly Val Gly Val Pro Gly Ala Gly Ala Gly Ser Gly
            515                 520                 525
Ala Gly Ala Gly Ser Gly Ala Gly Ala Gly Ser Gly Ala Gly Ala Gly
            530                 535                 540
Ser Gly Val Gly Val Pro Gly Val Gly Val Pro Gly Val Gly Val Pro
545                 550                 555                 560
Gly Val Gly Val Pro Gly Lys Gly Val Pro Gly Val Gly Val Pro Gly
            565                 570                 575
Val Gly Val Pro Gly Val Gly Val Pro Gly Ala Gly Ala Gly Ser Gly
            580                 585                 590
```

-continued

Ala Gly Ala Gly Ser Gly Ala Gly Ser Gly Ala Gly
            595             600             605

Ser Gly Val Gly Val Pro Gly Val Gly Val Pro Gly Val Gly Val Pro
610             615             620

Gly Val Gly Val Pro Gly Lys Gly Val Pro Gly Val Gly Val Pro Gly
625             630             635             640

Val Gly Val Pro Gly Val Gly Val Pro Gly Ala Gly Ala Gly Ser Gly
            645             650             655

Ala Gly Ala Gly Ser Gly Ala Gly Ser Gly Ala Gly Ala Gly
            660             665             670

Ser Gly Val Gly Val Pro Gly Val Gly Val Pro Gly Val Gly Val Pro
            675             680             685

Gly Val Gly Val Pro Gly Lys Gly Val Pro Gly Val Gly Val Pro Gly
            690             695             700

Val Gly Val Pro Gly Val Gly Val Pro Gly Ala Gly Ala Gly Ser Gly
705             710             715             720

Ala Gly Ala Gly Ser Gly Ala Gly Ala Gly Ser Gly Ala Gly Ala Gly
            725             730             735

Ser Gly Val Gly Val Pro Gly Val Gly Val Pro Gly Val Gly Val Pro
            740             745             750

Gly Val Gly Val Pro Gly Lys Gly Val Pro Gly Val Gly Val Pro Gly
            755             760             765

Val Gly Val Pro Gly Val Gly Val Pro Gly Ala Gly Ala Gly Ser Gly
            770             775             780

Ala Gly Ala Gly Ser Gly Ala Gly Ala Gly Ser Gly Ala Gly Ala Gly
785             790             795             800

Ser Gly Val Gly Val Pro Gly Val Gly Val Pro Gly Val Gly Val Pro
            805             810             815

Gly Val Gly Val Pro Gly Lys Gly Val Pro Gly Val Gly Val Pro Gly
            820             825             830

Val Gly Val Pro Gly Val Gly Val Pro Gly Ala Gly Ala Gly Ser Gly
            835             840             845

Ala Gly Ala Gly Ser Gly Ala Gly Ala Met Asp Pro Gly Arg Tyr Gln
850             855             860

Asp Leu Arg Ser His His His His His His
865             870

<210> SEQ ID NO 23
<211> LENGTH: 938
<212> TYPE: PRT
<213> ORGANISM: Artificial Sequence
<220> FEATURE:
<223> OTHER INFORMATION: SELP0K

<400> SEQUENCE: 23

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
            35                  40                  45

Gly Val Gly Val Pro Gly Lys Gly Val Pro Gly Val Gly Val Pro Gly
            50                  55                  60

Val Gly Val Pro Gly Val Gly Val Pro Gly Ala Gly Ala Gly Ser Gly
65              70                  75                  80

-continued

```
Ala Gly Ala Gly Ser Gly Val Gly Val Pro Gly Val Gly Val Pro Gly
                85                  90                  95
Val Gly Val Pro Gly Val Gly Val Pro Gly Lys Gly Val Pro Gly Val
            100                 105                 110
Gly Val Pro Gly Val Gly Val Pro Gly Val Gly Val Pro Gly Ala Gly
        115                 120                 125
Ala Gly Ser Gly Ala Gly Ala Gly Ser Gly Val Gly Val Pro Gly Val
    130                 135                 140
Gly Val Pro Gly Val Gly Val Pro Gly Val Gly Val Pro Gly Lys Gly
145                 150                 155                 160
Val Pro Gly Val Gly Val Pro Gly Val Gly Val Pro Gly Val Gly Val
                165                 170                 175
Pro Gly Ala Gly Ala Gly Ser Gly Ala Gly Ala Gly Ser Gly Val Gly
            180                 185                 190
Val Pro Gly Val Gly Val Pro Gly Val Gly Val Pro Gly Val Gly Val
        195                 200                 205
Pro Gly Lys Gly Val Pro Gly Val Gly Val Pro Gly Val Gly Val Pro
    210                 215                 220
Gly Val Gly Val Pro Gly Ala Gly Ala Gly Ser Gly Ala Gly Ala Gly
225                 230                 235                 240
Ser Gly Val Gly Val Pro Gly Val Gly Val Pro Gly Val Gly Val Pro
                245                 250                 255
Gly Val Gly Val Pro Gly Lys Gly Val Pro Gly Val Gly Val Pro Gly
            260                 265                 270
Val Gly Val Pro Gly Val Gly Val Pro Gly Ala Gly Ala Gly Ser Gly
        275                 280                 285
Ala Gly Ala Gly Ser Gly Val Gly Val Pro Gly Val Gly Val Pro Gly
    290                 295                 300
Val Gly Val Pro Gly Val Gly Val Pro Gly Lys Gly Val Pro Gly Val
305                 310                 315                 320
Gly Val Pro Gly Val Gly Val Pro Gly Val Gly Val Pro Gly Ala Gly
                325                 330                 335
Ala Gly Ser Gly Ala Gly Ala Gly Ser Gly Val Gly Val Pro Gly Val
            340                 345                 350
Gly Val Pro Gly Val Gly Val Pro Gly Val Gly Val Pro Gly Lys Gly
        355                 360                 365
Val Pro Gly Val Gly Val Pro Gly Val Gly Val Pro Gly Val Gly Val
    370                 375                 380
Pro Gly Ala Gly Ala Gly Ser Gly Ala Gly Ala Gly Ser Gly Val Gly
385                 390                 395                 400
Val Pro Gly Val Gly Val Pro Gly Val Gly Val Pro Gly Val Gly Val
                405                 410                 415
Pro Gly Lys Gly Val Pro Gly Val Gly Val Pro Gly Val Gly Val Pro
            420                 425                 430
Gly Val Gly Val Pro Gly Ala Gly Ala Gly Ser Gly Ala Gly Ala Gly
        435                 440                 445
Ser Gly Val Gly Val Pro Gly Val Gly Val Pro Gly Val Gly Val Pro
    450                 455                 460
Gly Val Gly Val Pro Gly Lys Gly Val Pro Gly Val Gly Val Pro Gly
465                 470                 475                 480
Val Gly Val Pro Gly Val Gly Val Pro Gly Ala Gly Ala Gly Ser Gly
                485                 490                 495
```

-continued

```
Ala Gly Ala Gly Ser Gly Val Gly Val Pro Gly Val Gly Val Pro Gly
                500                 505                 510
Val Gly Val Pro Gly Val Gly Val Pro Gly Lys Gly Val Pro Gly Val
            515                 520                 525
Gly Val Pro Gly Val Gly Val Pro Gly Val Gly Val Pro Gly Ala Gly
        530                 535                 540
Ala Gly Ser Gly Ala Gly Ala Gly Ser Gly Val Gly Val Pro Gly Val
545                 550                 555                 560
Gly Val Pro Gly Val Gly Val Pro Gly Val Gly Val Pro Gly Lys Gly
                565                 570                 575
Val Pro Gly Val Gly Val Pro Gly Val Gly Val Pro Gly Val Gly Val
            580                 585                 590
Pro Gly Ala Gly Ala Gly Ser Gly Ala Gly Ala Gly Ser Gly Val Gly
        595                 600                 605
Val Pro Gly Val Gly Val Pro Gly Val Gly Val Pro Gly Val Gly Val
        610                 615                 620
Pro Gly Lys Gly Val Pro Gly Val Gly Val Pro Gly Val Gly Val Pro
625                 630                 635                 640
Gly Val Gly Val Pro Gly Ala Gly Ala Gly Ser Gly Ala Gly Ala Gly
                645                 650                 655
Ser Gly Val Gly Val Pro Gly Val Gly Val Pro Gly Val Gly Val Pro
            660                 665                 670
Gly Val Gly Val Pro Gly Lys Gly Val Pro Gly Val Gly Val Pro Gly
        675                 680                 685
Val Gly Val Pro Gly Val Gly Val Pro Gly Ala Gly Ala Gly Ser Gly
        690                 695                 700
Ala Gly Ala Gly Ser Gly Val Gly Val Pro Gly Val Gly Val Pro Gly
705                 710                 715                 720
Val Gly Val Pro Gly Val Gly Val Pro Gly Lys Gly Val Pro Gly Val
                725                 730                 735
Gly Val Pro Gly Val Gly Val Pro Gly Val Gly Val Pro Gly Ala Gly
            740                 745                 750
Ala Gly Ser Gly Ala Gly Ala Gly Ser Gly Val Gly Val Pro Gly Val
        755                 760                 765
Gly Val Pro Gly Val Gly Val Pro Gly Val Gly Val Pro Gly Lys Gly
        770                 775                 780
Val Pro Gly Val Gly Val Pro Gly Val Gly Val Pro Gly Val Gly Val
785                 790                 795                 800
Pro Gly Ala Gly Ala Gly Ser Gly Ala Gly Ala Gly Ser Gly Val Gly
                805                 810                 815
Val Pro Gly Val Gly Val Pro Gly Val Gly Val Pro Gly Val Gly Val
            820                 825                 830
Pro Gly Lys Gly Val Pro Gly Val Gly Val Pro Gly Val Gly Val Pro
        835                 840                 845
Gly Val Gly Val Pro Gly Ala Gly Ala Gly Ser Gly Ala Gly Ala Gly
        850                 855                 860
Ser Gly Val Gly Val Pro Gly Val Gly Val Pro Gly Val Gly Val Pro
865                 870                 875                 880
Gly Val Gly Val Pro Gly Lys Gly Val Pro Gly Val Gly Val Pro Gly
                885                 890                 895
Val Gly Val Pro Gly Val Gly Val Pro Gly Ala Gly Ala Gly Ser Gly
            900                 905                 910
```

Ala Gly Ala Gly Ser Gly Ala Gly Ala Met Asp Pro Gly Arg Tyr Gln
            915                 920                 925

Asp Leu Arg Ser His His His His His His
    930                 935

<210> SEQ ID NO 24
<211> LENGTH: 60
<212> TYPE: PRT
<213> ORGANISM: Artificial Sequence
<220> FEATURE:
<223> OTHER INFORMATION: Repeat sequence

<400> SEQUENCE: 24

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro
    50                  55                  60

<210> SEQ ID NO 25
<211> LENGTH: 886
<212> TYPE: PRT
<213> ORGANISM: Artificial Sequence
<220> FEATURE:
<223> OTHER INFORMATION: SELP415K

<400> SEQUENCE: 25

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Lys Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Ala Gly
        115                 120                 125

Ala Gly Ser Gly Ala Gly Ala Gly Ser Gly Ala Gly Ala Gly Ser Gly
    130                 135                 140

Ala Gly Ala Gly Ser Gly Val Gly Val Pro Gly Val Gly Val Pro Gly
145                 150                 155                 160

Val Gly Val Pro Gly Val Gly Val Pro Gly Lys Gly Val Pro Gly Val
                165                 170                 175

Gly Val Pro Gly Val Gly Val Pro Gly Val Gly Val Pro Gly Val Gly
            180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Ala Gly Ala Gly Ser Gly Ala Gly Ala Gly
225                 230                 235                 240

Ser Gly Ala Gly Ala Gly Ser Gly Ala Gly Ala Gly Ser Gly Val Gly
                245                 250                 255

Val Pro Gly Val Gly Val Pro Gly Val Gly Val Pro Gly Val Gly Val
                260                 265                 270

Pro Gly Lys Gly Val Pro Gly Val Gly Val Pro Gly Val Gly Val Pro
            275                 280                 285

Gly Val Gly Val Pro Gly Val Gly Val Pro Gly Val Gly Val Pro Gly
            290                 295                 300

Val Gly Val Pro Gly Val Gly Val Pro Gly Val Gly Val Pro Gly Val
305                 310                 315                 320

Gly Val Pro Gly Val Gly Val Pro Gly Val Gly Val Pro Gly Ala Gly
                325                 330                 335

Ala Gly Ser Gly Ala Gly Ala Gly Ser Gly Ala Gly Ala Gly Ser Gly
                340                 345                 350

Ala Gly Ala Gly Ser Gly Val Gly Val Pro Gly Val Gly Val Pro Gly
            355                 360                 365

Val Gly Val Pro Gly Val Gly Val Pro Gly Lys Gly Val Pro Gly Val
            370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
                405                 410                 415

Pro Gly Val Gly Val Pro Gly Val Gly Val Pro Gly Val Gly Val Pro
            420                 425                 430

Gly Val Gly Val Pro Gly Ala Gly Ala Gly Ser Gly Ala Gly Ala Gly
            435                 440                 445

Ser Gly Ala Gly Ala Gly Ser Gly Ala Gly Ala Gly Ser Gly Val Gly
450                 455                 460

Val Pro Gly Val Gly Val Pro Gly Val Gly Val Pro Gly Val Gly Val
465                 470                 475                 480

Pro Gly Lys Gly Val Pro Gly Val Gly Val Pro Gly Val Gly Val Pro
            485                 490                 495

Gly Val Gly Val Pro Gly Val Gly Val Pro Gly Val Gly Val Pro Gly
            500                 505                 510

Val Gly Val Pro Gly Val Gly Val Pro Gly Val Gly Val Pro Gly Val
            515                 520                 525

Gly Val Pro Gly Val Gly Val Pro Gly Val Gly Val Pro Gly Ala Gly
            530                 535                 540

Ala Gly Ser Gly Ala Gly Ala Gly Ser Gly Ala Gly Ala Gly Ser Gly
545                 550                 555                 560

Ala Gly Ala Gly Ser Gly Val Gly Val Pro Gly Val Gly Val Pro Gly
                565                 570                 575

Val Gly Val Pro Gly Val Gly Val Pro Gly Lys Gly Val Pro Gly Val
                580                 585                 590

Gly Val Pro Gly Val Gly Val Pro Gly Val Gly Val Pro Gly Val Gly
            595                 600                 605

Val Pro Gly Val Gly Val Pro Gly Val Gly Val Pro Gly Val Gly Val
            610                 615                 620

Pro Gly Val Gly Val Pro Gly Val Gly Val Pro Gly Val Gly Val Pro
625                 630                 635                 640

Gly Val Gly Val Pro Gly Ala Gly Ala Gly Ser Gly Ala Gly Ala Gly
            645                 650                 655

Ser Gly Ala Gly Ala Gly Ser Gly Ala Gly Ala Gly Ser Gly Val Gly
            660                 665                 670

Val Pro Gly Val Gly Val Pro Gly Val Gly Val Pro Gly Val Gly Val
            675                 680                 685

Pro Gly Lys Gly Val Pro Gly Val Gly Val Pro Gly Val Gly Val Pro
            690                 695                 700

Gly Val Gly Val Pro Gly Val Gly Val Pro Gly Val Gly Val Pro Gly
705                 710                 715                 720

Val Gly Val Pro Gly Val Gly Val Pro Gly Val Gly Val Pro Gly Val
            725                 730                 735

Gly Val Pro Gly Val Gly Val Pro Gly Val Gly Val Pro Gly Ala Gly
            740                 745                 750

Ala Gly Ser Gly Ala Gly Ala Gly Ser Gly Ala Gly Ala Gly Ser Gly
            755                 760                 765

Ala Gly Ala Gly Ser Gly Val Gly Val Pro Gly Val Gly Val Pro Gly
            770                 775                 780

Val Gly Val Pro Gly Val Gly Val Pro Gly Lys Gly Val Pro Gly Val
785                 790                 795                 800

Gly Val Pro Gly Val Gly Val Pro Gly Val Gly Val Pro Gly Val Gly
            805                 810                 815

Val Pro Gly Val Gly Val Pro Gly Val Gly Val Pro Gly Val Gly Val
            820                 825                 830

Pro Gly Val Gly Val Pro Gly Val Gly Val Pro Gly Val Gly Val Pro
            835                 840                 845

Gly Val Gly Val Pro Gly Ala Gly Ala Gly Ser Gly Ala Gly Ala Gly
            850                 855                 860

Ser Gly Ala Gly Ala Met Asp Pro Gly Arg Tyr Gln Asp Leu Arg Ser
865                 870                 875                 880

His His His His His His
            885

<210> SEQ ID NO 26
<211> LENGTH: 750
<212> TYPE: PRT
<213> ORGANISM: Artificial Sequence
<220> FEATURE:
<223> OTHER INFORMATION: SELP815K

<400> SEQUENCE: 26

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
            35                  40                  45

Val Pro Gly Val Gly Val Pro Gly Val Gly Val Pro Gly Val Gly Val
            50                  55                  60

Pro Gly Lys Gly Val Pro Gly Val Gly Val Pro Gly Val Gly Val Pro
65                  70                  75                  80

Gly Val Gly Val Pro Gly Val Gly Val Pro Gly Val Gly Val Pro Gly
            85                  90                  95

Val Gly Val Pro Gly Val Gly Val Pro Gly Val Gly Val Pro Gly Val
            100                 105                 110

```
Gly Val Pro Gly Val Gly Val Pro Gly Val Gly Val Pro Gly Ala Gly
            115                 120                 125
Ala Gly Ser Gly Ala Gly Ser Gly Ala Gly Ala Gly Ser Gly
        130                 135                 140
Ala Gly Ala Gly Ser Gly Ala Gly Ser Gly Ala Gly Ala Gly
145                 150                 155                 160
Ser Gly Val Gly Val Pro Gly Val Gly Val Pro Gly Val Gly Val Pro
                165                 170                 175
Gly Val Gly Val Pro Gly Lys Gly Val Pro Gly Val Gly Val Pro Gly
            180                 185                 190
Val Gly Val Pro Gly Val Gly Val Pro Gly Val Gly Val Pro Gly Val
        195                 200                 205
Gly Val Pro Gly Val Gly Val Pro Gly Val Gly Val Pro Gly Val Gly
    210                 215                 220
Val Pro Gly Val Gly Val Pro Gly Val Gly Val Pro Gly Val Gly Val
225                 230                 235                 240
Pro Gly Ala Gly Ala Gly Ser Gly Ala Gly Ala Gly Ser Gly Ala Gly
                245                 250                 255
Ala Gly Ser Gly Ala Gly Ser Gly Ala Gly Ala Gly Ser Gly
            260                 265                 270
Ala Gly Ala Gly Ser Gly Val Gly Val Pro Gly Val Gly Val Pro Gly
        275                 280                 285
Val Gly Val Pro Gly Val Gly Val Pro Gly Lys Gly Val Pro Gly Val
    290                 295                 300
Gly Val Pro Gly Val Gly Val Pro Gly Val Gly Val Pro Gly Val Gly
305                 310                 315                 320
Val Pro Gly Val Gly Val Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Ala Gly Ala Gly Ser Gly Ala Gly Ala Gly
        355                 360                 365
Ser Gly Ala Gly Ala Gly Ser Gly Ala Gly Ala Gly Ser Gly Ala Gly
    370                 375                 380
Ala Gly Ser Gly Ala Gly Ala Gly Ser Gly Val Gly Val Pro Gly Val
385                 390                 395                 400
Gly Val Pro Gly Val Gly Val Pro Gly Val Gly Val Pro Gly Lys Gly
                405                 410                 415
Val Pro Gly Val Gly Val Pro Gly Val Gly Val Pro Gly Val Gly Val
            420                 425                 430
Pro Gly Val Gly Val Pro Gly Val Gly Val Pro Gly Val Gly Val Pro
        435                 440                 445
Gly Val Gly Val Pro Gly Val Gly Val Pro Gly Val Gly Val Pro Gly
    450                 455                 460
Val Gly Val Pro Gly Val Gly Val Pro Gly Ala Gly Ala Gly Ser Gly
465                 470                 475                 480
Ala Gly Ala Gly Ser Gly Ala Gly Ala Gly Ser Gly Ala Gly Ala Gly
                485                 490                 495
Ser Gly Ala Gly Ala Gly Ser Gly Ala Gly Ala Gly Ser Gly Val Gly
            500                 505                 510
Val Pro Gly Val Gly Val Pro Gly Val Gly Val Pro Gly Val Gly Val
        515                 520                 525
```

```
Pro Gly Lys Gly Val Pro Gly Val Gly Val Pro Gly Val Gly Val Pro
    530                 535                 540

Gly Val Gly Val Pro Gly Val Gly Val Pro Gly Val Gly Val Pro Gly
545                 550                 555                 560

Val Gly Val Pro Gly Val Gly Val Pro Gly Val Gly Val Pro Gly Val
                565                 570                 575

Gly Val Pro Gly Val Gly Val Pro Gly Val Gly Val Pro Gly Ala Gly
            580                 585                 590

Ala Gly Ser Gly Ala Gly Ala Gly Ser Gly Ala Gly Ala Gly Ser Gly
        595                 600                 605

Ala Gly Ala Gly Ser Gly Ala Gly Ala Gly Ser Gly Ala Gly Ala Gly
    610                 615                 620

Ser Gly Val Gly Val Pro Gly Val Gly Val Pro Gly Val Gly Val Pro
625                 630                 635                 640

Gly Val Gly Val Pro Gly Lys Gly Val Pro Gly Val Gly Val Pro Gly
                645                 650                 655

Val Gly Val Pro Gly Val Gly Val Pro Gly Val Gly Val Pro Gly Val
            660                 665                 670

Gly Val Pro Gly Val Gly Val Pro Gly Val Gly Val Pro Gly Val Gly
        675                 680                 685

Val Pro Gly Val Gly Val Pro Gly Val Gly Val Pro Gly Val Gly Val
    690                 695                 700

Pro Gly Ala Gly Ala Gly Ser Gly Ala Gly Ala Gly Ser Gly Ala Gly
705                 710                 715                 720

Ala Gly Ser Gly Ala Gly Ala Gly Ser Gly Ala Gly Ala Met Asp Pro
                725                 730                 735

Gly Arg Tyr Gln Asp Leu Arg Ser His His His His His His
            740                 745                 750

<210> SEQ ID NO 27
<211> LENGTH: 36
<212> TYPE: PRT
<213> ORGANISM: Artificial Sequence
<220> FEATURE:
<223> OTHER INFORMATION: Repeat sequence

<400> SEQUENCE: 27

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser
        35

<210> SEQ ID NO 28
<211> LENGTH: 54
<212> TYPE: PRT
<213> ORGANISM: Artificial Sequence
<220> FEATURE:
<223> OTHER INFORMATION: Repeat sequence

<400> SEQUENCE: 28

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
                35                  40                  45
```

Gly Ala Gly Ala Gly Ser
            50

<210> SEQ ID NO 29
<211> LENGTH: 852
<212> TYPE: PRT
<213> ORGANISM: Artificial Sequence
<220> FEATURE:
<223> OTHER INFORMATION: Repeat sequence

<400> SEQUENCE: 29

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Val Thr Gly Arg Gly Asp Ser
    50                  55                  60

Pro Ala Ser Ala Ala Gly Tyr Gly Ala Gly Ala Gly Ser Gly Ala Gly
65                  70                  75                  80

Ala Gly Ser Gly Ala Gly Ala Gly Ser Gly Ala Gly Ala Gly Ser Gly
                85                  90                  95

Ala Gly Ala Gly Ser Gly Ala Gly Ala Gly Ser Gly Ala Gly Ala Gly
            100                 105                 110

Ser Gly Ala Gly Ala Gly Ser Gly Ala Gly Ala Gly Ser Gly Ala Ala
        115                 120                 125

Val Thr Gly Arg Gly Asp Ser Pro Ala Ser Ala Ala Gly Tyr Gly Ala
    130                 135                 140

Gly Ala Gly Ser Gly Ala Gly Ala Gly Ser Gly Ala Gly Ala Gly Ser
145                 150                 155                 160

Gly Ala Gly Ala Gly Ser Gly Ala Gly Ala Gly Ser Gly Ala Gly Ala
                165                 170                 175

Gly Ser Gly Ala Gly Ala Gly Ser Gly Ala Gly Ala Gly Ser Gly Ala
            180                 185                 190

Gly Ala Gly Ser Gly Ala Ala Val Thr Gly Arg Gly Asp Ser Pro Ala
        195                 200                 205

Ser Ala Ala Gly Tyr Gly Ala Gly Ala Gly Ser Gly Ala Gly Ala Gly
    210                 215                 220

Ser Gly Ala Gly Ala Gly Ser Gly Ala Gly Ala Gly Ser Gly Ala Gly
225                 230                 235                 240

Ala Gly Ser Gly Ala Gly Ala Gly Ser Gly Ala Gly Ala Gly Ser Gly
                245                 250                 255

Ala Gly Ala Gly Ser Gly Ala Gly Ala Gly Ser Gly Ala Ala Val Thr
            260                 265                 270

Gly Arg Gly Asp Ser Pro Ala Ser Ala Ala Gly Tyr Gly Ala Gly Ala
        275                 280                 285

Gly Ser Gly Ala Gly Ala Gly Ser Gly Ala Gly Ala Gly Ser Gly Ala
    290                 295                 300

Gly Ala Gly Ser Gly Ala Gly Ala Gly Ser Gly Ala Gly Ala Gly Ser
305                 310                 315                 320

Gly Ala Gly Ala Gly Ser Gly Ala Gly Ala Gly Ser Gly Ala Gly Ala
                325                 330                 335

Gly Ser Gly Ala Ala Val Thr Gly Arg Gly Asp Ser Pro Ala Ser Ala
            340                 345                 350

```
Ala Gly Tyr Gly Ala Gly Ala Gly Ser Gly Ala Gly Ser Gly
        355                 360                 365
Ala Gly Ala Gly Ser Gly Ala Gly Ala Gly Ser Gly Ala Gly
        370                 375                 380
Ser Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Ala Val Thr Gly Arg
                405                 410                 415
Gly Asp Ser Pro Ala Ser Ala Ala Gly Tyr Gly Ala Gly Ala Gly Ser
                420                 425                 430
Gly Ala Gly Ala Gly Ser Gly Ala Gly Ala Gly Ser Gly Ala Gly Ala
        435                 440                 445
Gly Ser Gly Ala Gly Ala Gly Ser Gly Ala Gly Ala Gly Ser Gly Ala
450                 455                 460
Gly Ala Gly Ser Gly Ala Gly Ala Gly Ser Gly Ala Gly Ala Gly Ser
465                 470                 475                 480
Gly Ala Ala Val Thr Gly Arg Gly Asp Ser Pro Ala Ser Ala Ala Gly
                485                 490                 495
Tyr Gly Ala Gly Ala Gly Ser Gly Ala Gly Ala Gly Ser Gly Ala Gly
        500                 505                 510
Ala Gly Ser Gly Ala Gly Ala Gly Ser Gly Ala Gly Ala Gly Ser Gly
        515                 520                 525
Ala Gly Ala Gly Ser Gly Ala Gly Ala Gly Ser Gly Ala Gly Ala Gly
        530                 535                 540
Ser Gly Ala Gly Ala Gly Ser Gly Ala Ala Val Thr Gly Arg Gly Asp
545                 550                 555                 560
Ser Pro Ala Ser Ala Ala Gly Tyr Gly Ala Gly Ala Gly Ser Gly Ala
                565                 570                 575
Gly Ala Gly Ser Gly Ala Gly Ala Gly Ser Gly Ala Gly Ala Gly Ser
                580                 585                 590
Gly Ala Gly Ala Gly Ser Gly Ala Gly Ala Gly Ser Gly Ala Gly Ala
        595                 600                 605
Gly Ser Gly Ala Gly Ala Gly Ser Gly Ala Gly Ala Gly Ser Gly Ala
        610                 615                 620
Ala Val Thr Gly Arg Gly Asp Ser Pro Ala Ser Ala Ala Gly Tyr Gly
625                 630                 635                 640
Ala Gly Ala Gly Ser Gly Ala Gly Ala Gly Ser Gly Ala Gly Ala Gly
                645                 650                 655
Ser Gly Ala Gly Ala Gly Ser Gly Ala Gly Ala Gly Ser Gly Ala Gly
                660                 665                 670
Ala Gly Ser Gly Ala Gly Ala Gly Ser Gly Ala Gly Ala Gly Ser Gly
        675                 680                 685
Ala Gly Ala Gly Ser Gly Ala Ala Val Thr Gly Arg Gly Asp Ser Pro
        690                 695                 700
Ala Ser Ala Ala Gly Tyr Gly Ala Gly Ala Gly Ser Gly Ala Gly Ala
705                 710                 715                 720
Gly Ser Gly Ala Gly Ala Gly Ser Gly Ala Gly Ala Gly Ser Gly Ala
                725                 730                 735
Gly Ala Gly Ser Gly Ala Gly Ala Gly Ser Gly Ala Gly Ala Gly Ser
                740                 745                 750
Gly Ala Gly Ala Gly Ser Gly Ala Gly Ala Gly Ser Gly Ala Ala Val
        755                 760                 765
```

```
Thr Gly Arg Gly Asp Ser Pro Ala Ser Ala Ala Gly Tyr Gly Ala Gly
    770             775                 780

Ala Gly Ser Gly Ala Gly Ala Gly Ser Gly Ala Gly Ala Gly Ser Gly
785                 790                 795                 800

Ala Gly Ala Gly Ser Gly Ala Gly Ala Gly Ser Gly Ala Gly Ala Gly
                805                 810                 815

Ser Gly Ala Gly Ala Gly Ser Gly Ala Gly Ala Gly Ser Gly Ala Gly
            820                 825                 830

Ala Gly Ser Gly Ala Ala Val Thr Gly Arg Gly Asp Ser Pro Ala Ser
        835                 840                 845

Ala Ala Gly Tyr
    850

<210> SEQ ID NO 30
<211> LENGTH: 980
<212> TYPE: PRT
<213> ORGANISM: Artificial Sequence
<220> FEATURE:
<223> OTHER INFORMATION: PronectinF

<400> SEQUENCE: 30

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Gly Ala Gly Ser Gly Ala Gly
    50                  55                  60

Ala Gly Ser Gly Ala Gly Ala Gly Ser Gly Ala Ala Val Thr Gly Arg
65                  70                  75                  80

Gly Asp Ser Pro Ala Ser Ala Ala Gly Tyr Gly Ala Gly Ala Gly Ser
                85                  90                  95

Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Ala Gly Ala Ser Gly Ala Gly Ala Gly Ser
    130                 135                 140

Gly Ala Ala Val Thr Gly Arg Gly Asp Ser Pro Ala Ser Ala Ala Gly
145                 150                 155                 160

Tyr Gly Ala Gly Ala Gly Ser Gly Ala Gly Ala Gly Ser Gly Ala Gly
                165                 170                 175

Ala Gly Ser Gly Ala Gly Ala Gly Ser Gly Ala Gly Ala Gly Ser Gly
            180                 185                 190

Ala Gly Ala Gly Ser Gly Ala Gly Ala Gly Ser Gly Ala Gly Ala Gly
        195                 200                 205

Ser Gly Ala Gly Ala Gly Ser Gly Ala Ala Val Thr Gly Arg Gly Asp
    210                 215                 220

Ser Pro Ala Ser Ala Ala Gly Tyr Gly Ala Gly Ala Gly Ser Gly Ala
225                 230                 235                 240

Gly Ala Gly Ser Gly Ala Gly Ala Gly Ser Gly Ala Gly Ala Gly Ser
                245                 250                 255

Gly Ala Gly Ala Gly Ser Gly Ala Gly Ala Gly Ser Gly Ala Gly Ala
            260                 265                 270
```

```
Gly Ser Gly Ala Gly Ala Gly Ser Gly Ala Gly Ala Gly Ser Gly Ala
            275                 280                 285

Ala Val Thr Gly Arg Gly Asp Ser Pro Ala Ser Ala Ala Gly Tyr Gly
        290                 295                 300

Ala Gly Ala Gly Ser Gly Ala Gly Ala Gly Ser Gly Ala Gly Ala Gly
305                 310                 315                 320

Ser Gly Ala Gly Ala Gly Ser Gly Ala Gly Ala Gly Ser Gly Ala Gly
                325                 330                 335

Ala Gly Ser Gly Ala Gly Ala Gly Ser Gly Ala Gly Ala Gly Ser Gly
            340                 345                 350

Ala Gly Ala Gly Ser Gly Ala Ala Val Thr Gly Arg Gly Asp Ser Pro
            355                 360                 365

Ala Ser Ala Ala Gly Tyr Gly Ala Gly Ala Gly Ser Gly Ala Gly Ala
        370                 375                 380

Gly Ser Gly Ala Gly Ala Gly Ser Gly Ala Gly Ala Gly Ser Gly Ala
385                 390                 395                 400

Gly Ala Gly Ser Gly Ala Gly Ala Gly Ser Gly Ala Gly Ala Gly Ser
                405                 410                 415

Gly Ala Gly Ala Gly Ser Gly Ala Gly Ala Gly Ser Gly Ala Ala Val
            420                 425                 430

Thr Gly Arg Gly Asp Ser Pro Ala Ser Ala Ala Gly Tyr Gly Ala Gly
        435                 440                 445

Ala Gly Ser Gly Ala Gly Ala Gly Ser Gly Ala Gly Ala Gly Ser Gly
            450                 455                 460

Ala Gly Ala Gly Ser Gly Ala Gly Ala Gly Ser Gly Ala Gly Ala Gly
465                 470                 475                 480

Ser Gly Ala Gly Ala Gly Ser Gly Ala Gly Ala Gly Ser Gly Ala Gly
                485                 490                 495

Ala Gly Ser Gly Ala Ala Val Thr Gly Arg Gly Asp Ser Pro Ala Ser
            500                 505                 510

Ala Ala Gly Tyr Gly Ala Gly Ala Gly Ser Gly Ala Gly Ala Gly Ser
        515                 520                 525

Gly Ala Gly Ala Gly Ser Gly Ala Gly Ala Gly Ser Gly Ala Gly Ala
            530                 535                 540

Gly Ser Gly Ala Gly Ala Gly Ser Gly Ala Gly Ala Gly Ser Gly Ala
545                 550                 555                 560

Gly Ala Gly Ser Gly Ala Gly Ala Gly Ser Gly Ala Ala Val Thr Gly
                565                 570                 575

Arg Gly Asp Ser Pro Ala Ser Ala Ala Gly Tyr Gly Ala Gly Ala Gly
            580                 585                 590

Ser Gly Ala Gly Ala Gly Ser Gly Ala Gly Ala Gly Ser Gly Ala Gly
        595                 600                 605

Ala Gly Ser Gly Ala Gly Ala Gly Ser Gly Ala Gly Ala Gly Ser Gly
            610                 615                 620

Ala Gly Ala Gly Ser Gly Ala Gly Ala Gly Ser Gly Ala Gly Ala Gly
625                 630                 635                 640

Ser Gly Ala Ala Val Thr Gly Arg Gly Asp Ser Pro Ala Ser Ala Ala
                645                 650                 655

Gly Tyr Gly Ala Gly Ala Gly Ser Gly Ala Gly Ala Gly Ser Gly Ala
            660                 665                 670

Gly Ala Gly Ser Gly Ala Gly Ala Gly Ser Gly Ala Gly Ala Gly Ser
            675                 680                 685
```

-continued

Gly Ala Gly Ala Gly Ser Gly Ala Gly Ala Gly Ser Gly Ala Gly Ala
            690                 695                 700

Gly Ser Gly Ala Gly Ala Gly Ser Gly Ala Ala Val Thr Gly Arg Gly
705                 710                 715                 720

Asp Ser Pro Ala Ser Ala Ala Gly Tyr Gly Ala Gly Ala Gly Ser Gly
                725                 730                 735

Ala Gly Ala Gly Ser Gly Ala Gly Ala Gly Ser Gly Ala Gly Ala Gly
            740                 745                 750

Ser Gly Ala Gly Ala Gly Ser Gly Ala Gly Ala Gly Ser Gly Ala Gly
        755                 760                 765

Ala Gly Ser Gly Ala Gly Ala Gly Ser Gly Ala Gly Ala Gly Ser Gly
        770                 775                 780

Ala Ala Val Thr Gly Arg Gly Asp Ser Pro Ala Ser Ala Ala Gly Tyr
785                 790                 795                 800

Gly Ala Gly Ala Gly Ser Gly Ala Gly Ala Gly Ser Gly Ala Gly Ala
                805                 810                 815

Gly Ser Gly Ala Gly Ala Gly Ser Gly Ala Gly Ala Gly Ser Gly Ala
            820                 825                 830

Gly Ala Gly Ser Gly Ala Gly Ala Gly Ser Gly Ala Gly Ala Gly Ser
        835                 840                 845

Gly Ala Gly Ala Gly Ser Gly Ala Ala Val Thr Gly Arg Gly Asp Ser
850                 855                 860

Pro Ala Ser Ala Ala Gly Tyr Gly Ala Gly Ala Gly Ser Gly Ala Gly
865                 870                 875                 880

Ala Gly Ser Gly Ala Gly Ala Gly Ser Gly Ala Gly Ala Gly Ser Gly
                885                 890                 895

Ala Gly Ala Gly Ser Gly Ala Gly Ala Gly Ser Gly Ala Gly Ala Gly
            900                 905                 910

Ser Gly Ala Gly Ala Gly Ser Gly Ala Gly Ala Gly Ser Gly Ala Ala
        915                 920                 925

Val Thr Gly Arg Gly Asp Ser Pro Ala Ser Ala Ala Gly Tyr Gly Ala
        930                 935                 940

Gly Ala Gly Ser Gly Ala Gly Ala Gly Ser Gly Ala Gly Ala Met Asp
945                 950                 955                 960

Pro Gly Arg Tyr Gln Leu Ser Ala Gly Arg Tyr His Tyr Gln Leu Val
                965                 970                 975

Trp Cys Gln Lys
            980

<210> SEQ ID NO 31
<211> LENGTH: 888
<212> TYPE: PRT
<213> ORGANISM: Artificial Sequence
<220> FEATURE:
<223> OTHER INFORMATION: Repeat sequence

<400> SEQUENCE: 31

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

```
Ala Val Ser Ala Gly Pro Ser Ala Gly Tyr Gly Ala Gly Ala Gly Ser
 65                  70                  75                  80
Gly Ala Gly Ala Gly Ser Gly Ala Gly Ala Gly Ser Gly Ala Gly Ala
                 85                  90                  95
Gly Ser Gly Ala Gly Ala Gly Ser Gly Ala Gly Ala Gly Ser Gly Ala
            100                 105                 110
Gly Ala Gly Ser Gly Ala Gly Ala Gly Ser Gly Ala Gly Ala Gly Ser
            115                 120                 125
Gly Ala Ala Pro Gly Ala Ser Ile Lys Val Ala Val Ser Ala Gly Pro
            130                 135                 140
Ser Ala Gly Tyr Gly Ala Gly Ala Gly Ser Gly Ala Gly Ala Gly Ser
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
            180                 185                 190
Gly Ala Gly Ser Gly Ala Gly Ala Gly Ser Gly Ala Ala Pro Gly Ala
            195                 200                 205
Ser Ile Lys Val Ala Val Ser Ala Gly Pro Ser Ala Gly Tyr Gly Ala
            210                 215                 220
Gly Ala Gly Ser Gly Ala Gly Ala Gly Ser Gly Ala Gly Ala Gly Ser
225                 230                 235                 240
Gly Ala Gly Ala Gly Ser Gly Ala Gly Ala Gly Ser Gly Ala Gly Ala
                245                 250                 255
Gly Ser Gly Ala Gly Ala Gly Ser Gly Ala Gly Ala Gly Ser Gly Ala
            260                 265                 270
Gly Ala Gly Ser Gly Ala Ala Pro Gly Ala Ser Ile Lys Val Ala Val
            275                 280                 285
Ser Ala Gly Pro Ser Ala Gly Tyr Gly Ala Gly Ala Gly Ser Gly Ala
            290                 295                 300
Gly Ala Gly Ser Gly Ala Gly Ala Gly Ser Gly Ala Gly Ala Gly Ser
305                 310                 315                 320
Gly Ala Gly Ala Gly Ser Gly Ala Gly Ala Gly Ser Gly Ala Gly Ala
                325                 330                 335
Gly Ser Gly Ala Gly Ala Gly Ser Gly Ala Gly Ala Gly Ser Gly Ala
            340                 345                 350
Ala Pro Gly Ala Ser Ile Lys Val Ala Val Ser Ala Gly Pro Ser Ala
            355                 360                 365
Gly Tyr Gly Ala Gly Ala Gly Ser Gly Ala Gly Ala Gly Ser Gly Ala
            370                 375                 380
Gly Ala Gly Ser Gly Ala Gly Ala Gly Ser Gly Ala Gly Ala Gly Ser
385                 390                 395                 400
Gly Ala Gly Ala Gly Ser Gly Ala Gly Ala Gly Ser Gly Ala Gly Ala
                405                 410                 415
Gly Ser Gly Ala Gly Ala Gly Ser Gly Ala Ala Pro Gly Ala Ser Ile
            420                 425                 430
Lys Val Ala Val Ser Ala Gly Pro Ser Ala Gly Tyr Gly Ala Gly Ala
            435                 440                 445
Gly Ser Gly Ala Gly Ala Gly Ser Gly Ala Gly Ala Gly Ser Gly Ala
            450                 455                 460
Gly Ala Gly Ser Gly Ala Gly Ala Gly Ser Gly Ala Gly Ala Gly Ser
465                 470                 475                 480
```

```
Gly Ala Gly Ala Gly Ser Gly Ala Gly Ala Gly Ser Gly Ala Gly Ala
                485                 490                 495

Gly Ser Gly Ala Ala Pro Gly Ala Ser Ile Lys Val Ala Val Ser Ala
            500                 505                 510

Gly Pro Ser Ala Gly Tyr Gly Ala Gly Ala Gly Ser Gly Ala Gly Ala
            515                 520                 525

Gly Ser Gly Ala Gly Ala Gly Ser Gly Ala Gly Ala Gly Ser Gly Ala
            530                 535                 540

Gly Ala Gly Ser Gly Ala Gly Ser Gly Ala Gly Ala Gly Ser
545                 550                 555                 560

Gly Ala Gly Ala Gly Ser Gly Ala Gly Ala Gly Ser Gly Ala Ala Pro
            565                 570                 575

Gly Ala Ser Ile Lys Val Ala Val Ser Ala Gly Pro Ser Ala Gly Tyr
            580                 585                 590

Gly Ala Gly Ala Gly Ser Gly Ala Gly Ala Gly Ser Gly Ala Gly Ala
            595                 600                 605

Gly Ser Gly Ala Gly Ala Gly Ser Gly Ala Gly Ala Gly Ser Gly Ala
            610                 615                 620

Gly Ala Gly Ser Gly Ala Gly Ala Gly Ser Gly Ala Gly Ala Gly Ser
625                 630                 635                 640

Gly Ala Gly Ala Gly Ser Gly Ala Ala Pro Gly Ala Ser Ile Lys Val
            645                 650                 655

Ala Val Ser Ala Gly Pro Ser Ala Gly Tyr Gly Ala Gly Ala Gly Ser
            660                 665                 670

Gly Ala Gly Ala Gly Ser Gly Ala Gly Ala Gly Ser Gly Ala Gly Ala
            675                 680                 685

Gly Ser Gly Ala Gly Ala Gly Ser Gly Ala Gly Ala Gly Ser Gly Ala
            690                 695                 700

Gly Ala Gly Ser Gly Ala Gly Ala Gly Ser Gly Ala Gly Ala Gly Ser
705                 710                 715                 720

Gly Ala Ala Pro Gly Ala Ser Ile Lys Val Ala Val Ser Ala Gly Pro
            725                 730                 735

Ser Ala Gly Tyr Gly Ala Gly Ala Gly Ser Gly Ala Gly Ala Gly Ser
            740                 745                 750

Gly Ala Gly Ala Gly Ser Gly Ala Gly Ala Gly Ser Gly Ala Gly Ala
            755                 760                 765

Gly Ser Gly Ala Gly Ala Gly Ser Gly Ala Gly Ala Gly Ser Gly Ala
            770                 775                 780

Gly Ala Gly Ser Gly Ala Gly Ala Gly Ser Gly Ala Ala Pro Gly Ala
785                 790                 795                 800

Ser Ile Lys Val Ala Val Ser Ala Gly Pro Ser Ala Gly Tyr Gly Ala
            805                 810                 815

Gly Ala Gly Ser Gly Ala Gly Ala Gly Ser Gly Ala Gly Ala Gly Ser
            820                 825                 830

Gly Ala Gly Ala Gly Ser Gly Ala Gly Ala Gly Ser Gly Ala Gly Ala
            835                 840                 845

Gly Ser Gly Ala Gly Ala Gly Ser Gly Ala Gly Ala Gly Ser Gly Ala
            850                 855                 860

Gly Ala Gly Ser Gly Ala Ala Pro Gly Ala Ser Ile Lys Val Ala Val
865                 870                 875                 880

Ser Ala Gly Pro Ser Ala Gly Tyr
            885
```

<210> SEQ ID NO 32
<211> LENGTH: 1019
<212> TYPE: PRT
<213> ORGANISM: Artificial Sequence
<220> FEATURE:
<223> OTHER INFORMATION: PronectinL

<400> SEQUENCE: 32

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Gly Ala Gly Ser Gly Ala Gly
    50                  55                  60

Ala Gly Ser Gly Ala Gly Ala Gly Ser Gly Ala Ala Pro Gly Ala Ser
65                  70                  75                  80

Ile Lys Val Ala Val Ser Ala Gly Pro Ser Ala Gly Tyr Gly Ala Gly
                85                  90                  95

Ala Gly Ser Gly Ala Gly Ala Gly Ser Gly Ala Gly Ala Gly Ser Gly
            100                 105                 110

Ala Gly Ala Gly Ser Gly Ala Gly Ala Gly Ser Gly Ala Gly Ala Gly
        115                 120                 125

Ser Gly Ala Gly Ala Gly Ser Gly Ala Gly Ala Gly Ser Gly Ala Gly
    130                 135                 140

Ala Gly Ser Gly Ala Ala Pro Gly Ala Ser Ile Lys Val Ala Val Ser
145                 150                 155                 160

Ala Gly Pro Ser Ala Gly Tyr Gly Ala Gly Ala Gly Ser Gly Ala Gly
                165                 170                 175

Ala Gly Ser Gly Ala Gly Ala Gly Ser Gly Ala Gly Ala Gly Ser Gly
            180                 185                 190

Ala Gly Ala Gly Ser Gly Ala Gly Ala Gly Ser Gly Ala Gly Ala Gly
        195                 200                 205

Ser Gly Ala Gly Ala Gly Ser Gly Ala Gly Ala Gly Ser Gly Ala Ala
    210                 215                 220

Pro Gly Ala Ser Ile Lys Val Ala Val Ser Ala Gly Pro Ser Ala Gly
225                 230                 235                 240

Tyr Gly Ala Gly Ala Gly Ser Gly Ala Gly Ala Gly Ser Gly Ala Gly
                245                 250                 255

Ala Gly Ser Gly Ala Gly Ala Gly Ser Gly Ala Gly Ala Gly Ser Gly
            260                 265                 270

Ala Gly Ala Gly Ser Gly Ala Gly Ala Gly Ser Gly Ala Gly Ala Gly
        275                 280                 285

Ser Gly Ala Gly Ala Gly Ser Gly Ala Ala Pro Gly Ala Ser Ile Lys
    290                 295                 300

Val Ala Val Ser Ala Gly Pro Ser Ala Gly Tyr Gly Ala Gly Ala Gly
305                 310                 315                 320

Ser Gly Ala Gly Ala Gly Ser Gly Ala Gly Ala Gly Ser Gly Ala Gly
                325                 330                 335

Ala Gly Ser Gly Ala Gly Ala Gly Ser Gly Ala Gly Ala Gly Ser Gly
            340                 345                 350

Ala Gly Ala Gly Ser Gly Ala Gly Ala Gly Ser Gly Ala Gly Ala Gly
        355                 360                 365
```

```
Ser Gly Ala Ala Pro Gly Ala Ser Ile Lys Val Ala Val Ser Ala Gly
    370                 375                 380
Pro Ser Ala Gly Tyr Gly Ala Gly Ala Gly Ser Gly Ala Gly Ala Gly
385                 390                 395                 400
Ser Gly Ala Gly Ala Gly Ser Gly Ala Gly Ala Gly Ser Gly Ala Gly
                    405                 410                 415
Ala Gly Ser Gly Ala Gly Ala Gly Ser Gly Ala Gly Ala Gly Ser Gly
                420                 425                 430
Ala Gly Ala Gly Ser Gly Ala Gly Ala Gly Ser Gly Ala Ala Pro Gly
            435                 440                 445
Ala Ser Ile Lys Val Ala Val Ser Ala Gly Pro Ser Ala Gly Tyr Gly
    450                 455                 460
Ala Gly Ala Gly Ser Gly Ala Gly Ala Gly Ser Gly Ala Gly Ala Gly
465                 470                 475                 480
Ser Gly Ala Gly Ala Gly Ser Gly Ala Gly Ala Gly Ser Gly Ala Gly
                    485                 490                 495
Ala Gly Ser Gly Ala Gly Ala Gly Ser Gly Ala Gly Ala Gly Ser Gly
                500                 505                 510
Ala Gly Ala Gly Ser Gly Ala Ala Pro Gly Ala Ser Ile Lys Val Ala
            515                 520                 525
Val Ser Ala Gly Pro Ser Ala Gly Tyr Gly Ala Gly Ala Gly Ser Gly
    530                 535                 540
Ala Gly Ala Gly Ser Gly Ala Gly Ala Gly Ser Gly Ala Gly Ala Gly
545                 550                 555                 560
Ser Gly Ala Gly Ala Gly Ser Gly Ala Gly Ala Gly Ser Gly Ala Gly
                    565                 570                 575
Ala Gly Ser Gly Ala Gly Ala Gly Ser Gly Ala Gly Ala Gly Ser Gly
                580                 585                 590
Ala Ala Pro Gly Ala Ser Ile Lys Val Ala Val Ser Ala Gly Pro Ser
            595                 600                 605
Ala Gly Tyr Gly Ala Gly Ala Gly Ser Gly Ala Gly Ala Gly Ser Gly
    610                 615                 620
Ala Gly Ala Gly Ser Gly Ala Gly Ala Gly Ser Gly Ala Gly Ala Gly
625                 630                 635                 640
Ser Gly Ala Gly Ala Gly Ser Gly Ala Gly Ala Gly Ser Gly Ala Gly
                    645                 650                 655
Ala Gly Ser Gly Ala Gly Ala Gly Ser Gly Ala Ala Pro Gly Ala Ser
                660                 665                 670
Ile Lys Val Ala Val Ser Ala Gly Pro Ser Ala Gly Tyr Gly Ala Gly
    675                 680                 685
Ala Gly Ser Gly Ala Gly Ala Gly Ser Gly Ala Gly Ala Gly Ser Gly
690                 695                 700
Ala Gly Ala Gly Ser Gly Ala Gly Ala Gly Ser Gly Ala Gly Ala Gly
705                 710                 715                 720
Ser Gly Ala Gly Ala Gly Ser Gly Ala Gly Ala Gly Ser Gly Ala Gly
                    725                 730                 735
Ala Gly Ser Gly Ala Ala Pro Gly Ala Ser Ile Lys Val Ala Val Ser
                740                 745                 750
Ala Gly Pro Ser Ala Gly Tyr Gly Ala Gly Ala Gly Ser Gly Ala Gly
            755                 760                 765
Ala Gly Ser Gly Ala Gly Ala Gly Ser Gly Ala Gly Ala Gly Ser Gly
        770                 775                 780
```

Ala Gly Ala Gly Ser Gly Ala Gly Ala Gly Ser Gly Ala Gly
785                 790                 795                 800

Ser Gly Ala Gly Ala Gly Ser Gly Ala Gly Ala Gly Ser Gly Ala Ala
                805                 810                 815

Pro Gly Ala Ser Ile Lys Val Ala Val Ser Ala Gly Pro Ser Ala Gly
            820                 825                 830

Tyr Gly Ala Gly Ala Gly Ser Gly Ala Gly Ala Gly Ser Gly Ala Gly
            835                 840                 845

Ala Gly Ser Gly Ala Gly Ala Gly Ser Gly Ala Gly Ala Gly Ser Gly
        850                 855                 860

Ala Gly Ala Gly Ser Gly Ala Gly Ala Gly Ser Gly Ala Gly Ala Gly
865                 870                 875                 880

Ser Gly Ala Gly Ala Gly Ser Gly Ala Ala Pro Gly Ala Ser Ile Lys
                885                 890                 895

Val Ala Val Ser Ala Gly Pro Ser Ala Gly Tyr Gly Ala Gly Ala Gly
            900                 905                 910

Ser Gly Ala Gly Ala Gly Ser Gly Ala Gly Ala Gly Ser Gly Ala Gly
        915                 920                 925

Ala Gly Ser Gly Ala Gly Ala Gly Ser Gly Ala Gly Ala Gly Ser Gly
        930                 935                 940

Ala Gly Ala Gly Ser Gly Ala Gly Ala Gly Ser Gly Ala Gly Ala Gly
945                 950                 955                 960

Ser Gly Ala Ala Pro Gly Ala Ser Ile Lys Val Ala Val Ser Ala Gly
                965                 970                 975

Pro Ser Ala Gly Tyr Gly Ala Gly Ala Gly Ser Gly Ala Gly Ala Gly
            980                 985                 990

Ser Gly Ala Gly Ala Met Asp Pro Gly Arg Tyr Gln Leu Ser Ala Gly
        995                 1000                1005

Arg Tyr His Tyr Gln Leu Val Trp Cys Gln Lys
    1010                1015

<210> SEQ ID NO 33
<211> LENGTH: 436
<212> TYPE: PRT
<213> ORGANISM: Oryctolagus cuniculus

<400> SEQUENCE: 33

Met Asp Pro Met Leu Thr Gln Thr Pro Ala Ser Val Ser Ala Ala Val
1               5                   10                  15

Gly Gly Thr Val Thr Ile Lys Cys Gln Ala Ser Glu Asn Ile Tyr Thr
            20                  25                  30

Ser Leu Ala Trp Tyr Gln Gln Lys Pro Gly His Ser Pro Lys Leu Leu
        35                  40                  45

Ile Tyr Ser Ala Ser Thr Leu Ala Ser Gly Val Ala Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Gln Cys Ser Ala Tyr Gly Arg
                85                  90                  95

Ser Gly Asn Ser Phe Gly Gly Thr Glu Val Val Val Asn Gly Asp
            100                 105                 110

Pro Val Ala Pro Thr Val Leu Ile Phe Pro Pro Ala Ala Asp Gln Val
        115                 120                 125

Ala Thr Gly Thr Val Thr Ile Val Cys Val Ala Asn Lys Tyr Phe Pro
    130                 135                 140

Asp Val Thr Val Thr Trp Glu Val Asp Gly Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Asn Arg Gly Asp Cys Met Gln Ser Leu Glu Glu Ser Gly Gly Arg
    210                 215                 220

Leu Val Thr Pro Gly Thr Pro Leu Thr Leu Thr Cys Thr Val Ser Gly
225                 230                 235                 240

Ile Asp Leu Ser Arg Tyr Ala Met Gly Trp Val Arg Gln Ala Pro Gly
                245                 250                 255

Lys Gly Leu Glu Trp Ile Ala Met Ile Asn Gly Tyr Gly Thr Thr Tyr
            260                 265                 270

Tyr Ala Ser Trp Ala Lys Gly Arg Phe Thr Ile Ser Arg Thr Ser Thr
        275                 280                 285

Thr Val Asp Leu Lys Ile Thr Ser Pro Thr Thr Glu Asp Thr Ala Thr
    290                 295                 300

Tyr Phe Cys Val Arg Tyr Pro Glu Ser Ser Ser Met Phe Asp Leu Trp
305                 310                 315                 320

Gly Gln Gly Thr Leu Val Thr Val Ser Ser Gly Gln Pro Lys Ala Pro
                325                 330                 335

Ser Val Phe Pro Leu Ala Pro Cys Cys Gly Asp Thr Pro Ser Ser Thr
            340                 345                 350

Val Thr Leu Gly Cys Leu Val Lys Gly Tyr Leu Pro Glu Pro Val Thr
        355                 360                 365

Val Thr Trp Asn Ser Gly Thr Leu Thr Asn Gly Val Arg Thr Phe Pro
    370                 375                 380

Ser Val Arg Gln Ser Ser Gly Leu Tyr Ser Leu Ser Ser Val Val Ser
385                 390                 395                 400

Val Thr Ser Ser Ser Gln Pro Val Thr Cys Asn Val Ala His Pro Ala
                405                 410                 415

Thr Asn Thr Lys Val Asp Lys Thr Val Ala Pro Ser Thr Cys Ser Lys
            420                 425                 430

Pro Thr Cys Pro
        435

<210> SEQ ID NO 34
<211> LENGTH: 605
<212> TYPE: PRT
<213> ORGANISM: Aspergillus niger

<400> SEQUENCE: 34

Met Gln Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Asp Val Ser Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asn Ile Ser Val Leu Val Ile Glu Ser Gly Ser Tyr Glu Ser Asp Arg
65                  70                  75                  80

```
Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Thr Trp Thr Arg Pro His Lys Ala Gln Val Asp Ser Trp
130                 135                 140

Glu Thr Val Phe Gly Asn Gly Trp Asn Trp Asp Asn Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Val Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
210                 215                 220

Asp Phe Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Gln Tyr Val
            260                 265                 270

Gly Lys Val Leu Leu Ser Gln Asn Gly Thr Thr Pro Arg Ala Val Gly
        275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ala Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ser
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Ala Leu Leu Ile
                405                 410                 415

Gln Tyr Glu Asn Tyr Arg Asp Trp Ile Val Asn His Asn Val Ala Tyr
            420                 425                 430

Ser Glu Leu Phe Leu Asp Thr Ala Gly Val Ala Ser Phe Asp Val Trp
        435                 440                 445

Asp Leu Leu Pro Phe Thr Arg Gly Tyr Val His Ile Leu Asp Lys Asp
450                 455                 460

Pro Tyr Leu His His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495
```

```
Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Thr Glu Tyr
        515                 520                 525

Ile Pro Tyr His Phe Arg Pro Asn Tyr His Gly Val Gly Thr Cys Ser
    530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
                580                 585                 590

Ile Ser Asp Ala Ile Leu Glu Asp Tyr Ala Ser Met Gln
                595                 600                 605

<210> SEQ ID NO 35
<211> LENGTH: 607
<212> TYPE: PRT
<213> ORGANISM: Bos taurus

<400> SEQUENCE: 35

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270
```

-continued

```
Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
                340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Glu Cys Cys
        370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
        530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
            595                 600                 605
```

METHOD FOR PRODUCING PROTEIN COMPOSITION, AND PROTEIN COMPOSITION

TECHNICAL FIELD

The present invention relates to a method for producing a protein composition and a protein composition.

BACKGROUND ART

Proteins for use in medical applications and biochemical applications need to be sterilized before use. Sterilization is achieved by ethylene oxide gas sterilization, filtration sterilization, or radiosterilization. Radiosterilization is advantageous in terms of the absence of toxic residues (ethylene oxide gas) after sterilization as well as cost and validation.

Radiosterilization of proteins unfortunately causes changes such as degradation and denaturation. Such changes in proteins are induced by reactions of active radicals (hydroxy radicals, oxygen radicals) generated by radiation with the proteins.

Conventionally, the following methods have been employed in order to suppress changes in proteins induced by active radicals: a method in which proteins are irradiated with radiation under cooling conditions; a method in which water is removed from a radiation irradiation target; and a method in which a radical scavenger against active radicals is added (Patent Literatures 1 and 2).

Yet, the method in which proteins are irradiated with radiation under cooling conditions is not very effective, and the production cost for cooling is high. In addition, when sterilizing a highly hydrophilic protein or a protein that undergoes denaturation by complete removal of water, it is difficult to remove water from a radiation irradiation target. Further, in the case where a radical scavenger is used to prevent changes in proteins induced by active radicals, the radical scavenger needs to be added in a large amount, which unfortunately impairs physiological and physicochemical functions of the proteins.

CITATION LIST

Patent Literature

Patent Literature 1: JP-T 2003-527210
Patent Literature 2: JP-T 2010-514747

SUMMARY OF INVENTION

Technical Problem

The present invention aims to provide a method for producing a protein composition, the method being capable of suppressing changes such as degradation and denaturation of a protein which occur when a highly hydrophilic protein or a protein that undergoes denaturation by complete removal of water is irradiated with radiation.

Solution to Problem

As a result of extensive studies, the present inventors arrived at the present invention. Specifically, the present invention is directed to a method for producing a protein composition containing a protein (A), a radical scavenger (RS), and at least one hydrogen-bond-formable compound (HC) selected from the group consisting of amino acids, peptides, and proteins other than the protein (A), the method including a sterilization step of radiosterilizing an unsterilized protein composition, wherein the unsterilized protein composition contains the protein (A), the radical scavenger (RS), and the hydrogen-bond-formable compound (HC), the protein (A) contains at least one functional group selected from the group consisting of sulfide, amide, hydroxyl, amino, and carboxyl groups, the hydrogen-bond-formable compound (HC) contains at least one functional group selected from the group consisting of sulfide, amide, hydroxyl, amino, and carboxyl groups, the at least one functional group in the protein (A) is capable of binding to the at least one functional group in the hydrogen-bond-formable compound (HC) via a hydrogen bond, the unsterilized protein composition has a water content of 0 to 30% by weight based on the weight of the unsterilized protein composition, a weight ratio of the radical scavenger (RS) to the protein (A) in the unsterilized protein composition [radical scavenger (RS)/protein (A)] is 0.01 to 1, and a molar ratio of a total molar number of functional groups in the hydrogen-bond-formable compound (HC) to a total molar number of functional groups in the protein (A) in the unsterilized protein composition [the total molar number of functional groups in the hydrogen-bond-formable compound (HC)/the total molar number of functional groups in the protein (A)] is 0.01 to 0.5.

The present invention also relates to a protein composition containing a protein (A), wherein the protein composition further contains a radical scavenger (RS), and at least one hydrogen-bond-formable compound (HC) selected from the group consisting of amino acids, peptides, and proteins other than the protein (A), the protein (A) contains at least one functional group selected from the group consisting of sulfide, amide, hydroxyl, amino, and carboxyl groups, the hydrogen-bond-formable compound (HC) contains at least one functional group selected from the group consisting of sulfide, amide, hydroxyl, amino, and carboxyl groups, the at least one functional group in the protein (A) is capable of binding to the at least one functional group in the hydrogen-bond-formable compound (HC) via a hydrogen bond, a weight ratio of the radical scavenger (RS) to the protein (A) in the protein composition [radical scavenger (RS)/protein (A)] is 0.01 to 1.0, a molar ratio of a total molar number of functional groups in the hydrogen-bond-formable compound (HC) to a total molar number of functional groups in the protein (A) in the protein composition [the total molar number of functional groups in the hydrogen-bond-formable compound (HC)/the total molar number of functional groups in the protein (A)] is 0.01 to 0.50, and the protein composition has been radiosterilized.

Advantageous Effects of Invention

According to the production method of the present invention, the addition amount of the radical scavenger (RS) can be reduced by effective scavenging of radicals generated when a highly hydrophilic protein or a protein that undergoes denaturation by complete removal of water is irradiated with radiation. Thus, physiological and physicochemical functions of the protein before being irradiated with radiation are maintained in a protein composition produced by the production method of the present invention.

DESCRIPTION OF EMBODIMENTS

In the method for producing a protein composition of the present invention, an unsterilized protein composition to be sterilized contains a protein (A), a radical scavenger (RS), and at least one hydrogen-bond-formable compound (HC) selected from the group consisting of amino acids, peptides, and proteins other than the protein (A).

The term "unsterilized protein composition" as used in the method for producing a protein composition of the present invention refers to a protein composition containing the protein (A), the radical scavenger (RS), and the hydrogen-bond-formable compound (HC) before being subjected to a sterilization step of the method for producing a protein composition of the present invention.

Examples of the protein (A) include animal-derived proteins, plant-derived proteins, microorganism-derived proteins, and recombinant proteins.

Examples of animal-derived proteins include protein formulations, enzymes, antibodies, coagulation factors, and extracellular matrices.

Examples of plant-derived proteins include enzymes and extracellular matrices.

Examples of microorganism-derived proteins include enzymes and extracellular matrices.

Examples of recombinant proteins include protein formulations and vaccines.

Examples of protein formulations include interferon α, interferon 13, interleukin 1 to 12, growth hormone, erythropoietin, insulin, granulocyte-colony stimulating factor (G-CSF), tissue plasminogen activator (TPA), natriuretic peptide, blood coagulation factor VIII, somatomedin, glucagon, growth hormone releasing factor, serum albumin, and calcitonin.

Examples of vaccines include hepatitis A vaccine, hepatitis B vaccine, and hepatitis C vaccine.

Examples of enzymes include hydrolases, isomerases, oxidoreductases, transferases, synthases, and lyases.

Examples of hydrolases include protease, serine protease, amylase, lipase, cellulase, and glucoamylase.

Examples of isomerases include glucose isomerase.

Examples of oxidoreductases include peroxidase.

Examples of transferases include acyltransferase and sulfotransferase.

Examples of synthases include fatty acid synthase, phosphate synthase, and citrate synthase.

Examples of lyases include pectin lyase.

Examples of antibodies include IgD, IgE, IgG, IgA, and IgM.

Examples of coagulation factors include fibrinogen, fibrin, prothrombin, thrombin, factor III, factor V, factor VII, factor VIII, factor IX, factor X, factor XII, and factor XIII.

Examples of extracellular matrices include collagen, fibronectin, laminin, and elastin.

The protein (A) contains at least one functional group selected from the group consisting of sulfide, amide, hydroxyl, amino, and carboxyl groups.

Preferred among these are hydroxyl, amide, amino, and carboxyl groups in terms of the hydrogen bond distance between the protein (A) and the hydrogen-bond-formable compound (HC).

The protein (A) containing at least one functional group selected from the group consisting of sulfide, amide, hydroxyl, amino, and carboxyl groups preferably contains an amino acid having the at least one functional group.

Examples of amino acids having a sulfide group include methionine and cysteine.

Examples of amide groups include an amide group formed by a peptide bond between amino acids contained in the protein (A).

Examples of amino acids having a hydroxyl group include serine, threonine, and tyrosine.

Examples of amino acids having an amino group include arginine, asparagine, glutamine, histidine, lysine, and tryptophan.

Examples of amino acids having a carboxyl group include aspartic acid and glutamic acid.

In terms of stability of the protein (A), the protein (A) is preferably one containing methionine, cysteine, serine, threonine, tyrosine, arginine, asparagine, glutamine, histidine, lysine, tryptophan, aspartic acid, and glutamic acid, more preferably one containing methionine, serine, threonine, tyrosine, arginine, asparagine, glutamine, histidine, lysine, tryptophan, aspartic acid, and glutamic acid.

In the method for producing a protein composition of the present invention, the protein (A) preferably contains a repetitive sequence (X) in terms of stability of the protein.

In the method for producing a protein composition of the present invention, the repetitive sequence (X) preferably includes any one amino acid sequence (a1) selected from the group consisting of GAGAGS (SEQ ID NO:1), RGD, YIGSR (SEQ ID NO:2), GVGVP (SEQ ID NO3), PGVGV (SEQ ID NO:4), VPGVG (SEQ ID NO:5), GVPGV (SEQ ID NO:6), VGVPG (SEQ ID NO:7), GPP, GAP, GAHGPAGPK (SEQ ID NO:8), GAA, VAAGY (SEQ ID NO:9), GAGAGAS (SEQ ID NO:10), LGPLGP (SEQ ID NO:11), GAHGPAGPK (SEQ ID NO:12), GAPGPAGPPGSRGDPGPP (SEQ ID NO:13), GAQGPAGPG (SEQ ID NO:14), GAPGAPGSQGAPGLQ (SEQ ID NO:15), GAPGTPGPQGLPGSP (SEQ ID NO:16), GAAVTGRGDSPASAAGY (SEQ ID NO:17), and GAAP-GASIKVAVSAGPSAGY (SEQ ID NO:18). The repetitive sequence (X) may include one or two or more of these amino acid sequences (a1).

In terms of stability of the protein, preferred among these are GAGAGS (SEQ ID NO:1), GAA, VAAGY (SEQ ID NO:9), and GAGAGAS (SEQ ID NO:10).

In the method for producing a protein composition of the present invention, in terms of stability of the protein, the repetitive sequence (X) includes preferably 2 to 200, more preferably 15 to 150, particularly preferably 30 to 120 units of GAGAGS (SEQ ID NO:1).

In the method for producing a protein composition of the present invention, in terms of stability of the protein, the repetitive sequence (X) preferably includes a sequence (Y) consisting of 2 to 200 repeats of an amino acid sequence (a2) that is one of GVGVP (SEQ ID NO:3), PGVGV (SEQ ID NO:4), VPGVG (SEQ ID NO:5), GVPGV (SEQ ID NO:6), VGVPG (SEQ ID NO7), GPP, GAP, or GAHGPAGPK (SEQ ID NO:8) and/or a sequence (Y1) in which 1 to 100 amino acids in the sequence (Y) are replaced by lysine (K) or arginine (R).

In terms of stability of the protein, the sequence (Y) is particularly preferably a sequence consisting of 2 to 200 repeats of GVGVP (SEQ ID NO:3), PGVGV (SEQ ID NO:4), VPGVG (SEQ ID NO:5), GVPGV (SEQ ID NO:6), or VGVPG (SEQ ID NO:7).

In addition, the repetitive sequence (X) may include one or two or more of these sequences (Y) and (Y1).

In the method for producing a protein composition of the present invention, a ratio of a number of units of GAGAGS (SEQ ID NO:1) to a total number of the amino acid sequences (a2) and amino acid sequences (a2') described below in one molecule of the protein (A) [(the number of units of GAGAGS (SEQ ID NO:1)):(the total number of the amino acid sequences (a2) and (a2'))] is preferably [1:2] to [1:20], more preferably [1:10] to [1:5], in terms of stability of the protein, amino acid sequence (a2'): an amino acid sequence in which one to five amino acids in the amino acid sequence (a2) are replaced by lysine (K) or arginine (R).

In the method for producing a protein composition of the present invention, in terms of bioactivity of the protein, the repetitive sequence (X) preferably includes a sequence (Y2) consisting of 1 to 50 repeats of an amino acid sequence (a3) that is one of GAAVTGRGDSPASAAGY (SEQ ID NO:17) or GAAPGASIKVAVSAGPSAGY (SEQ ID NO18).

In addition, the repetitive sequence (X) may include one or two or more of these sequences (Y2).

In the method for producing a protein composition of the present invention, the protein (A) may contain amino acids immediately upstream and downstream of the repetitive sequence (X) and between the repetitive sequences (X). In terms of solubility (solubility particularly in water) of the protein (A) and gelation time, the number of amino acids immediately upstream and downstream of the repetitive sequence (X) and between the repetitive sequences (X) is preferably 1 to 100, more preferably 5 to 40, particularly preferably 10 to 35.

Examples of the amino acids immediately upstream and downstream of the repetitive sequence (X) and between the repetitive sequences (X) include β-galactosidase-derived sequences and purified tags (e.g., 6xHis tag, V5 tag, Xpress tag, AU1 tag, T7 tag, VSV-G tag, DDDDK tag, S tag, CruzTag 09™, CruzTag$_{22™}$ CruzTag$_{41™}$, Glu-Glu tag, Ha.11 tag, KT3 tag, maltose binding protein, HQ tag, Myc tag, HA tag, and FLAG tag).

Some of preferred examples of the protein (A) in the method for producing a protein composition of the present invention are listed below.

(1) Examples of proteins in which the repetitive sequence (X) consists of GAGAGS (SEQ ID NO:1) and the sequence (Y1) include the followings:

protein (SELP 8K) of a sequence (SEQ ID NO:22) having a molecular mass of about 70 kDa, consisting of 12 units of (GAGAGS)$_4$ (SEQ ID NO:19) consisting of four tandem repeats of GAGAGS (SEQ ID NO:1), 13 units of (GVGVP)$_4$GKGVP(GVGVP)$_3$ (SEQ ID NO:20) (Y1-1) in which one valine (V) residue in a repetitive sequence (Y-1) consisting of eight tandem repeats of GVGVP (SEQ ID NO3) is replaced by lysine (K), and one unit of (GAGAGS)$_2$ (SEQ ID NO:21) consisting of two tandem repeats of GAGAGS (SEQ ID NO:1), wherein these sequences are chemically bound to each other to form (GVGVP)$_4$GKGVP(GVGVP)$_3$ [(GAGAGS)$_4$(GVGVP)$_4$GKGVP(GVGVP)$_3$]$_{12}$ (GAGAGS)$_2$ (SEQ ID NO:22);

protein (SELP OK) of a sequence (SEQ ID NO:23) having a molecular mass of about 77 kDa, consisting of 17 units of (GVGVP)$_4$GKGVP(GVGVP)$_3$ (SEQ ID NO:20) and 17 units of (GAGAGS)$_2$ (SEQ ID NO:21), wherein these sequences are chemically bound to each other to form [(GVGVP)$_4$GKGVP(GVGVP)$_3$ (GAGAGS)$_2$]$_{17}$ (SEQ ID NO:23);

protein (SELP 415K) of a sequence (SEQ ID NO:25) having a molecular mass of about 71 kDa, consisting of 16 units of (GAGAGS)$_2$ (SEQ ID NO:21), and eight units of (GVGVP)$_4$GKGVP(GVGVP)$_{11}$ (SEQ ID NO:24) in which one valine (V) residue in a repetitive sequence (Y-2) consisting of 16 tandem units of GVGVP (SEQ ID NO:3) is replaced by lysine (K), wherein these sequences are chemically bound to each other to form [(GAGAGS)$_2$(GVGVP)$_4$GKGVP (GVGVP)$_{11}$(GAGAGS)$_2$]$_8$(SEQ ID NO:25); and protein (SELP 815K) of a sequence (SEQ ID NO:26) having a molecular mass of about 65 kDa, consisting of six units of (GAGAGS)$_2$ (SEQ ID NO:21), six units of (GVGVP)$_4$GKGVP(GVGVP)$_{11}$ (SEQ ID NO:24), and six units of (GAGAGS)$_4$ (SEQ ID NO:19), wherein these sequences are chemically bound to each other to form [(GAGAGS)$_2$(GVGVP)$_4$GKGVP (GVGVP)$_{11}$(GAGAGS)$_4$]$_6$(SEQ ID NO:26).

In terms of stability of the protein, the protein (A) is preferably SELP OK or SELP 8K, more preferably SELP 8K, among the above examples.

(2) Examples of proteins in which the repetitive sequence (X) consists of GAGAGS (SEQ ID NO:1) and the sequence (Y2) include the followings:

protein (ProNectin F) of a sequence (SEQ ID NO:30) having a molecular mass of about 73 kDa, consisting of one unit of (GAGAGS)$_6$ (SEQ ID NO:27) consisting of six tandem repeats of GAGAGS (SEQ ID NO:1), one unit of GAAVTGRGDSPASAAGY (SEQ ID NO:17), one unit of [(GAGAGS)$_9$(GAAVTGRGDSPASA-AGY)]$_{12}$ (SEQ ID NO:29) consisting of twelve tandem repeats of a sequence which is formed by GAAVT-GRGDSPASAAGY (SEQ ID NO:17) and (GAGAGS)$_9$ (SEQ ID NO:28) consisting of nine tandem repeats of GAGAGS (SEQ ID NO1), and one unit of (GAGAGS)$_2$ (SEQ ID NO:21), wherein these sequences are chemically bound to each other to form (GAGAGS)$_6$(GAAVTGRGD-SPASAAGY)[(GAGAGS)$_9$(GAAVTGRGD SPASAAGY)]$_{12}$(GAG AGS)$_2$ (SEQ ID NO:30); and protein (ProNectin L) of a sequence (SEQ ID NO:32) having a molecular mass of about 76 kDa, consisting of one unit of (GAGAGS)$_6$ (SEQ ID NO:27), one unit of GAAPGASIKVAVSAGPSAGY (SEQ ID NO:18), one unit of [(GAGAGS)$_9$(GAAPGASIKVAVSAGP-SAGY)]$_{12}$ (SEQ ID NO:31) consisting of twelve tandem repeats of a sequence which is formed by (GAGAGS)$_9$(SEQ ID NO:28) and GAAPGASIKVA-VSAGPSAGY (SEQ TD NO:18), and one unit of (GAGAGS)$_2$ (SEQ ID NO:21), wherein these sequences are chemically bound to each other to form (GAGAGS)$_6$(GAAPGASIKVAVSAGP-SAGY)[(GAGAGS)$_9$(GAAPGASIKVAVSAGP-SAGY)]$_{12}$(GAGAGS)$_2$ (SEQ ID NO:32).

In terms of stability of the protein (A), the amino acid composition of the protein (A) is preferably such that the number of proline (P) residues accounts for 1 to 50%, the number of serine (S) residues accounts for 1 to 50%, and the number of valine (V) residues accounts for 1 to 50%, based on the total number of amino acids in the protein (A). More preferably, the number of proline (P) residues accounts for 1 to 20%, the number of serine (S) residues accounts for 1 to 20%, and the number of valine (V) residues accounts for 1 to 30%.

In terms of solubility of the protein (A), the protein (A) content of the protein composition is preferably 50% by weight or less, more preferably 10% by weight or less, based on the weight of the protein composition.

In the method for producing a protein composition of the present invention, the protein (A) preferably has a molecular mass of 15 to 200 kDa as determined by SDS-polyacrylamide gel electrophoresis.

The molecular mass of the protein (A) is determined by a method in which test samples are isolated by SDS-polyacrylamide gel electrophoresis and the migration distance of each test sample is compared with that of the standard substance.

In the method for producing a protein composition of the present invention, in terms of stability of the protein (A), the radical scavenger (RS) in the protein composition is preferably at least one selected from the group consisting of oxygen-containing conjugated structures and nitrogen-containing conjugated structures.

In the method for producing a protein composition of the present invention, the radical scavenger (RS) preferably has a radical scavenging ability against diphenylpicrylhydrazyl radicals (DPPH radicals) of 0.01 to 90 mg Trolox eq/mg.

The DPPH radical scavenging ability can be measured by the method described in "Shokuhin kinosei hyoka manyuarushu dainishu (the second collection of food functionality evaluation manuals)", DPPH radical scavenging activity evaluation method, Tomoyuki Oki, (2008) pp. 71-78, and can be evaluated as trolox equivalent.

In addition, the radical scavenging ability against peroxy radicals, hydroxy radicals, 2,2'-azino-bis-(3-ethylbenzothiazoline-6-sulphonic acid) (ABTS) radicals, oxygen radicals, and alkyl radicals can be measured by a method such as superoxide dismutase assay (SOD assay), ABTS radical scavenging ability measurement method, potential antioxidant (PAO) measurement method, or EPR spin trapping method to set the radical scavenging ability to 0.01 mg Trolox eq/mg or more.

Examples of the radical scavenger (RS) include organic acids (e.g., ascorbic acid, erythorbic acid, uric acid, gallic acid, glutathione, phenolic acid, ellagic acid, and chlorogenic acid), glutathione, edaravone, polyphenols (e.g., flavonoid, phenolic acid, ellagic acid, lignan, curcumin, and coumarin), and phenolic compounds (e.g., vanillin, pyrogallol, dibutylhydroxytoluene, and butylhydroxyanisole).

In particular, in terms of miscibility between the protein (A) and the radical scavenger (RS), radical scavenging ability, and safety, the radical scavenger (RS) is preferably ascorbic acid, edaravone, vanillin, gallic acid, glutathione, or chlorogenic acid, more preferably ascorbic acid or edaravone.

In terms of solubility, the radical scavenger (RS) content of the unsterilized protein composition is preferably 40% by weight or less, more preferably 30% by weight or less, based on the weight of the unsterilized protein composition.

In the method for producing a protein composition of the present invention, the hydrogen-bond-formable compound (HC) contains at least one functional group selected from the group consisting of sulfide, amide, hydroxyl, amino, and carboxyl groups.

In terms of the hydrogen bond distance between the protein (A) and the hydrogen-bond-formable compound (HC), the hydrogen-bond-formable compound (HC) preferably contains at least one functional group selected from the group consisting of carboxyl, hydroxyl, and amino groups, among the above examples.

Examples of the hydrogen-bond-formable compound (HC) include amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, and their derivatives) and peptides (e.g., aspartame, vasopressin, glucagon, and selectin).

In terms of the hydrogen bond distance and miscibility between the protein (A) and the hydrogen-bond-formable compound (HC), the hydrogen-bond-formable compound (HC) is preferably tryptophan, tyrosine, or histidine, more preferably tryptophan, among the above examples.

In terms of solubility, the hydrogen-bond-formable compound (HC) content of the unsterilized protein composition is preferably 25% by weight or less, more preferably 10% by weight or less, based on the weight of the unsterilized protein composition.

In the method for producing a protein composition of the present invention, the water content of the unsterilized protein composition is 0 to 30% by weight based on the weight of the unsterilized protein composition. In terms of stability of the protein, the water content is preferably 0.01 to 30% by weight, more preferably 0.01 to 15% by weight.

In the method for producing a protein composition of the present invention, the unsterilized protein composition may be dried before the sterilization step.

Examples of the method of drying the unsterilized protein composition include freeze-drying and heat-drying.

The water content of the unsterilized protein composition can be measured as described below.

<Method for Measuring the Water Content of the Unsterilized Protein Composition>

An amount of 50 to 100 mg of the unsterilized protein composition is weighed in a glass vial. The weighed amount (Ws0), and the weight of the glass vial (Wb0) are recorded. A dryer is set to 100° C., and the glass vial containing the unsterilized protein composition is placed in the dryer when the temperature reaches 100° C. (The glass vial is uncapped.) Two hours later, the glass vial containing the unsterilized protein composition is taken out from the dryer, and is left to cool to room temperature in a desiccator. After cooling, the glass vial is capped, and the weight (W) is measured. Then, the water content of the unsterilized protein composition is calculated from the following formula (1).

$$(Ws0+Wb0-W)/Ws0 \times 100 = \text{Water content (\% by weight) of the unsterilized protein composition} \quad (1)$$

In the method for producing a protein composition of the present invention, a weight ratio of the radical scavenger (RS) to the protein (A) in the unsterilized protein composition [radical scavenger (RS)/protein (A)] is 0.01 to 1.0. In terms of maintenance of physiological and physicochemical functions of the protein (A), the weight ratio is preferably 0.01 to 0.1, more preferably 0.01 to 0.05.

In the method for producing a protein composition of the present invention, a molar ratio of a total molar number of functional groups in the hydrogen-bond-formable compound (HC) to a total molar number of functional groups in the protein (A) in the unsterilized protein composition [the total molar number of functional groups in the hydrogen-bond-formable compound (HC)/the total molar number of functional groups in the protein (A)] is 0.01 to 0.50. In terms of protection of protein properties, the molar ratio is preferably 0.01 to 0.50, more preferably 0.01 to 0.10, still more preferably 0.01 to 0.05.

If the molar ratio exceeds 1.0, disadvantages resulting from the radical scavenger (RS) (e.g., changes in physiological and physicochemical functions, changes in pH environment, increased costs, inflammation, and carcinogenesis) will increase.

If the molar ratio is less than 0.01, the protein (A) will be denatured to a greater degree.

The "functional groups in the protein (A)" used for the calculation of the molar ratio refers to the functional groups in the protein (A) which form hydrogen bonds with the functional groups in the hydrogen-bond-formable compound (HC). The "functional groups in the hydrogen-bond-formable compound (HC)" used for the calculation of the molar ratio refers to the functional groups in the hydrogen-bond-formable compound (HC) which forms hydrogen bonds with the functional groups in the protein (A).

In the method for producing a protein composition of the present invention, as described above, the protein (A) contains at least one functional group selected from the group consisting of sulfide, amide, hydroxyl, amino, and carboxyl groups.

In addition, in the method for producing a protein composition of the present invention, the at least one functional group in the protein (A) is capable of binding to the at least one functional group in the hydrogen-bond-formable compound (HC) via a hydrogen bond.

It is particularly preferred that the functional groups in the hydrogen-bond-formable compound (HC) can form hydrogen bonds with the functional groups in the amino acids in the protein (A) that is easily denatured when irradiated with radiation. The presence of the hydrogen-bond-formable compound (HC) in the unsterilized protein composition facilitates prevention of denaturation of the protein (A) in the sterilization step.

Examples of the amino acids in the protein (A) that is easily denatured when irradiated with radiation include serine and aspartic acid.

The functional groups of the protein (A) may be on side chains of the amino acids in the protein (A).

In the case where these functional groups are on the side chains of the amino acids, the functional groups on the side chains of the amino acids in the protein (A) are capable of binding to the functional groups of the hydrogen-bond-formable compound (HC) via first hydrogen bonds. In terms of radical scavenging properties, each first hydrogen bond has a distance of preferably 1.3 to 1.9 Å, more preferably 1.7 to 1.8 Å.

In addition, an amide group, which is one of the functional groups in the protein (A) and which is formed by a peptide bond, is also in the protein (A).

The amide group formed by a peptide bond in the protein (A) is capable of binding to the hydrogen-bond-formable compound (HC) via a second hydrogen bond. In terms of radical scavenging properties, the second hydrogen bond has a distance of preferably 1.3 to 1.9 Å, more preferably 1.7 to 1.8 Å.

The hydrogen bond distance is calculated using simulation software (Gaussian: Gaussian, Inc.).

When calculating the hydrogen bond distance by simulation software (Gaussian), an amino acid having a predetermined functional group is selected as a model compound for the compound having the predetermined functional group in the protein (A). Then, the hydrogen bond distance between the functional group in the amino acid and the functional group in the hydrogen-bond-formable compound (HC) can be determined by calculation.

The hydrogen bond distance between the functional group in the amino acid and the functional group in the hydrogen-bond-formable compound (HC) refers to the hydrogen bond distance that is optimized such that the energy between these functional groups is minimized.

In the method for producing a protein composition of the present invention, in the case where the first hydrogen bond has a distance of 1.3 to 1.9 Å and the second hydrogen bond has a distance of 1.3 to 1.9 Å, these distances are shorter than the typical hydrogen bond distance (2.4 to 3.3 Å).

Thus, the presence of the hydrogen-bond-formable compound (HC) in the unsterilized protein composition can suppress denaturation of the protein (A) by radiation in the sterilization step. This is presumably because the hydrogen-bond-formable compound (HC) fulfills the role of facilitating transfer of radicals from the protein (A) to the radical scavenger (RS) through hydrogen bonds. Due to this synergistic effect, it is possible to drastically reduce the addition amount of the radical scavenger (RS) (the amount is reduced to about one hundredth), compared to the case where an attempt is made to suppress denaturation only by the radical scavenger (RS). This reduces disadvantages (e.g., changes in physiological and physicochemical functions, changes in pH environment, increased costs, inflammation induced by a protein to be produced, and carcinogenic properties of a protein to be produced) resulting from the addition of a large amount of the radical scavenger (RS) to the unsterilized protein composition.

In addition, in the method for producing a protein composition of the present invention, the hydrogen-bond-formable compound (HC) preferably binds to the protein (A) only via hydrogen bonds.

In the case where a compound that forms a covalent bond with the protein (A) is used instead of the hydrogen-bond-formable compound (HC), such a compound can also exhibit an equivalent function (role of facilitating transfer radicals from the protein (A) to the radical scavenger (RS)) to that of the hydrogen-bond-formable compound (HC); however, formation of such a covalent bond unfortunately changes physical and physiological functions of the protein (A). In contrast, in the case where the hydrogen-bond-formable compound (HC) binds to the protein (A) only via hydrogen bonds without forming covalent bonds, the above described disadvantages (e.g., changes in physiological and physicochemical functions and changes in safety) are prevented.

As a method for adjusting the hydrogen bond distance between at least one functional group selected from the group consisting of sulfide, amide, hydroxyl, amino, and carboxyl groups in the protein (A) and the functional group in the hydrogen-bond-formable compound (HC), for example, various functional groups, proteins, and hydrogen-bond-formable compounds (HC) are selected such that the hydrogen bond distance between at least one functional group selected from the group consisting of hydroxyl, amino, and carboxyl groups in the protein (A) and the functional group in the hydrogen-bond-formable compound (HC) is within the numerical range of 1.3 to 1.9 Å.

In other words, in the method for producing a protein composition of the present invention, the hydrogen-bond-formable compounds (HC) are preferably selected according to the type and other properties of the protein (A).

The hydrogen-bond-formable compounds (HC) may be screened by a method such as screening (1) or screening (2) described below.

<Screening (1)>

First, the protein (A) is irradiated with radiation to sterilize the protein (A). Subsequently, an amino acid (a) modified in the protein (A) irradiated with radiation is identified. Subsequently, the hydrogen-bond-formable compounds (HC) may be screened with the above-described simulation software or the like, using the amino acid (a) before modification as a model compound for the compound having a functional group on a side chain of an amino acid in the protein (A).

The modified amino acid (α) can be identified by LC-MSMS analysis. The LC-MSMS analysis conditions are preferably the same as those for "LC-MSMS measurement" (described later) for the calculation of the modification rate of the protein (A) using LC-MSMS.

The compounds (HC) capable of forming the first hydrogen bond can be screened by the method described here.
<Screening (2)>

The hydrogen-bond-formable compounds (HC) may be screened with the above-described simulation software or the like, using alanylalanine as a model compound for the compound having an amide group formed by a peptide bond in the protein (A).

The compounds (HC) capable of forming the second hydrogen bond can be screened by the method described here.

In the method for producing a protein composition of the present invention, the unsterilized protein composition may contain optional additives, in addition to the protein (A), the radical scavenger (RS), and the hydrogen-bond-formable compound (HC).

Examples of optional additives include antioxidants, antiseptics, stabilizers, solubilizing agents, and buffer components.

The method for producing a protein composition of the present invention includes the sterilization step of radiosterilizing the unsterilized protein composition.

The method for producing a protein composition of the present invention may also include, before the sterilization step, an unsterilized protein composition preparation step of preparing an unsterilized protein composition, a freeze-drying step of freeze-drying the unsterilized protein composition, and a packing step of packing the unsterilized protein composition, as described below.

(Unsterilized protein composition preparation step)
Examples of methods for preparing the unsterilized protein composition include a method in which the hydrogen-bond-formable compound (HC), the radical scavenger (RS), and the protein (A) are dissolved in water at room temperature. Any sterile water may be used. Examples of methods for sterilizing water include a method for filtering water through a microfiltration membrane having a pore diameter of 0.2 μm or less, a method for filtering water through an ultrafiltration membrane, a method for filtering water through a reverse osmosis membrane, and a method for heat-sterilizing water in an autoclave at 121° C. for 20 minutes to obtain ion-exchanged water.

(Freeze-Drying Step)
Examples of methods for freeze-drying the unsterilized protein composition include a method in which the temperature is lowered to about −30° C. to −35° C. to freeze the unsterilized protein composition. Then, the pressure is reduced to a vacuum state and the temperature is raised to about −10° C. to −20° C. (a temperature at which the equilibrium water vapor pressure is equal to or higher than the degree of vacuum) to sublime water.

Facility conditions are listed below, as an example.
Facility: freeze dryer "FD-10BM" (Nihon Techno Service, Co., Ltd.)
Freezing conditions: −30° C. (15 h)
Primary drying conditions: −10° C. (72 h)
Secondary drying conditions: 10° C. (72 h)
Degree of vacuum: 1 Pa to 10 Pa (Packing Step)
In the method for producing a protein composition of the present invention, before the sterilization step, the unsterilized protein composition may be packed to be shielded from the outside.

Examples of methods for packing include a vacuum packing method.

(Sterilization Step)
In the method for producing a protein composition of the present invention, examples of methods for radiosterilizing the unsterilized protein composition in the sterilization step include methods such as γ-ray sterilization and electron beam sterilization under the following conditions.
Irradiation facility: SHI-ATEX Co., Ltd.
Irradiation dose: 25 to 27 kGy
Environmental temperature during irradiation: −10° C. to 10° C.

In addition, in the method for producing a protein composition of the present invention, the protein composition is preferably sterilized to SAL $10^{-6}$ in accordance with JIS T 0806-2:2010 or ISO 11137-2:2006 in the sterilization step.

In addition, in the method for producing a protein composition of the present invention, the sterilization step may be performed only once or several times.

According to the method for producing a protein composition of the present invention, it is possible to produce a protein composition having a low denaturation rate. In particular, "the denaturation rate calculated based on HPLC measurement" and "the denaturation rate of the produced protein composition calculated based on LC-MSMS measurement", which are measured by the following methods, can be reduced.

As used herein, the term "denaturation rate of the produced protein composition calculated based on HPLC measurement" refers to a numerical value calculated from the following formula (2), wherein M is the peak height of the unsterilized protein composition and N is the peak height of the produced protein composition, as determined by HPLC measurement of the unsterilized protein composition and the produced protein composition under the conditions described below.

$$\text{Denaturation rate (\%)}=[1-(N/M)]\times 100 \quad (2)$$

(HPLC Measurement)
The unsterilized protein composition or the produced protein composition is dissolved in deionized water (1 mL) to obtain a solution containing 1 mg of the protein (A), and the solution is filtered through a 0.45-μm filter to obtain a test sample.

The test sample is measured by HPLC (Shimadzu Corporation) under the following conditions.
Column: Jupiter C4
Mobile phase:
 A: 99.85% by weight of water+0.15% by weight of trichloroacetic acid
 B: 34% by weight of acetonitrile+65.85% by weight of water+0.15% by weight of trichloroacetic acid
 C: 80% by weight of acetonitrile+19.85% by weight of water+0.15% by weight of trichloroacetic acid
Flow rate: 1 mL/min
Mode: curved gradient mode (A/B=86/14 to A/B=20/80 to C=100)
Measurement wavelength: 214 nm Generally, proteins in a protein composition become hydrophilic when the protein composition is radiosterilized. Thus, the peak in HPLC analysis of the radiosterilized protein composition is broad and low. Conversely, if the percentage of denatured proteins is low, the peak in HPLC analysis is sharp and is not likely to be low.

As used herein, the term "denaturation rate of the produced protein composition calculated based on LC-MSMS measurement" refers to a numerical value calculated from the following formula (3), wherein $O_n$ is the concentration of each amino acid in the unsterilized protein composition, $P_n$ is the concentration of each amino acid in the produced protein composition, and Q is the number of types of amino acids measured, as determined by LC-MSMS measurement of the unsterilized protein composition and the produced protein composition under the conditions described below.

$$\text{Denaturation rate (\%)} = 1/Q \times \Sigma[1-(P_n/O_n)] \times 100 \tag{3}$$

(LC-MSMS Measurement)

The unsterilized protein composition or the produced protein composition is added to 6N hydrochloric acid (200 μL) to obtain a solution containing 1 mg of the protein (A), followed by degassing. The solution is degassed until foam is no longer formed, and then the protein (A) in the solution is hydrolyzed under vacuum sealed conditions at 110° C. for 22 hours. After hydrolysis, the solution is diluted in deionized water to 800 μL. The diluted solution is filtered through a 0.45-μm filter to obtain a test sample.

The test sample is measured by LC-MSMS (Shimadzu Corporation) under the following conditions.

Column: InertSustain C18 (GL Sciences Inc.)
Mobile phase:
A: 0.05 M aqueous solution of trifluoroacetic acid
B: Methanol
A/B=95/5 (V/V)
Flow rate: 0.2 mL/min
Ion source: ESI (+)
Measurement mode: MRM (MSMS)

The amino acid composition is determined from the elution time and the molecular weight of the standard sample (standard amino acid mixture: type H).

The method for producing a protein composition of the present invention is a method for producing a protein composition for use in medical applications and biochemical applications. The method is used to prevent radiosterilization-induced changes in proteins such as degradation and denaturation.

A protein composition produced by the method for producing a protein composition of the present invention is also encompassed by the present invention.

Specifically, the present invention is directed to a protein composition containing a protein (A), wherein the protein composition further contains a radical scavenger (RS), and at least one hydrogen-bond-formable compound (HC) selected from the group consisting of amino acids, peptides, and proteins other than the protein (A), the protein (A) contains at least one functional group selected from the group consisting of sulfide, amide, hydroxyl, amino, and carboxyl groups, the hydrogen-bond-formable compound (HC) contains at least one functional group selected from the group consisting of sulfide, amide, hydroxyl, amino, and carboxyl groups, the at least one functional group in the protein (A) is capable of binding to the at least one functional group in the hydrogen-bond-formable compound (HC) via a hydrogen bond, a weight ratio of the radical scavenger (RS) to the protein (A) in the protein composition [radical scavenger (RS)/protein (A)] is 0.01 to 1.0, a molar ratio of a total molar number of functional groups in the hydrogen-bond-formable compound (HC) to a total molar number of functional groups in the protein (A) in the protein composition [the total molar number of functional groups in the hydrogen-bond-formable compound (HC)/the total molar number of functional groups in the protein (A)] is 0.01 to 0.50, and the protein composition has been radiosterilized.

In the protein composition of the present invention, the weight ratio of the radical scavenger (RS) to the protein (A) in the protein composition [radical scavenger (RS)/protein (A)] is 0.01 to 1.0, preferably 0.01 to 0.1, more preferably 0.01 to 0.05.

As described above, the production of the protein composition of the present invention involves radiosterilization. When the weight ratio of the radical scavenger (RS) to the protein (A) in the protein composition [radical scavenger (RS)/protein (A)] is 0.01 to 1.0, radiosterilization is less likely to produce a denatured form of the protein (A), which facilitates maintenance of physiological and physicochemical functions of the protein (A).

In the protein composition of the present invention, the molar ratio of the total molar number of functional groups in the hydrogen-bond-formable compound (HC) to the total molar number of functional groups in the protein (A) in the protein composition [the total molar number of functional groups in the hydrogen-bond-formable compound (HC)/the total molar number of functional groups in the protein (A)] is 0.01 to 0.50, preferably 0.01 to 0.10, more preferably 0.01 to 0.05.

As described above, the production of the protein composition of the present invention involves radiosterilization.

When the molar ratio of the total molar number of functional groups in the hydrogen-bond-formable compound (HC) to the total molar number of functional groups in the protein (A) in the protein composition [the total molar number of functional groups in the hydrogen-bond-formable compound (HC)/the total molar number of functional groups in the protein (A)] is 0.01 to 0.50, disadvantages resulting from the radical scavenger (RS) (e.g., changes in physiological and physicochemical functions, changes in pH environment, increased costs, inflammation, and carcinogenesis) are reduced. In addition, when radiosterilization is performed, the protein (A) is less likely to be denatured. Therefore, physiological and physicochemical functions of the protein (A) can be maintained.

The protein composition of the present invention has been radiosterilized.

Thus, use of the protein composition of the present invention in medical applications and biochemical applications can suitably prevent contamination.

The protein composition of the present invention has been preferably radiosterilized at 25 to 27 kGy.

The protein composition of the present invention has been more preferably sterilized to SAL $10^{-6}$ in accordance with JIS T 0806-2:2010 or ISO 11137-2:2006. The protein composition of the present invention that has been sterilized as described above is also usable as a medicinal product.

In the protein composition of the present invention, the protein composition preferably has a water content of 0 to 30% by weight, more preferably 0.01 to 30% by weight, still more preferably 0.01 to 15% by weight, based on the weight of the protein composition.

When the water content of the protein composition is 0 to 30% by weight based on the weight of the protein composition, the protein (A) in the protein composition has higher stability.

The protein composition of the present invention is preferably packed, more preferably vacuum-packed.

The protein composition when packed is shielded from the outside, and is thus less susceptible to contamination.

EXAMPLES

The present invention is described in more detail below with reference to examples and comparative examples, but the present invention is not limited thereto.

(Provision of Radical Scavenger (RS))

Various radical scavengers (RS) shown in Table 1 were provided. Table 1 shows the radical scavenging ability and the structure of each radical scavenger.

TABLE 1

| Radical scavenger (RS) | Radical scavenging ability (mg Trolox eq/mg) | Structure of radical scavenger (RS) |
|---|---|---|
| Ascorbic acid | 48.00 | Oxygen-containing conjugated structure |
| Edaravone | 63.00 | Oxygen-containing conjugated structure Nitrogen-containing conjugated structure |
| Vanillin | 0.05 | Oxygen-containing conjugated structure |
| Catechin | 28.00 | Oxygen-containing conjugated structure |
| Gallic acid | 86.00 | Oxygen-containing conjugated structure |
| Glutathione | 0.15 | Nitrogen-containing conjugated structure Oxygen-containing conjugated structure |
| Chlorogenic acid | 0.76 | Oxygen-containing conjugated structure |

(Screening of Hydrogen-Bond-Formable Compounds (HC))

First, as the protein (A), each of SELP 8K (sequence (22)), ProNectin F (sequence (30)), ProNectin L (sequence (32)), HRP-conjugated rabbit antibody (sequence (33)), glucose oxidase (sequence (34)), and bovine serum albumin (sequence (35)) was dissolved in water and, and these aqueous solutions were each freeze-dried, followed by vacuum-packing in a nitrogen atmosphere. Each vacuum-packed protein (A) was irradiated with electron beam at 25 kGy at −20° C.

Subsequently, the amino acid composition of the protein (A) before electron beam irradiation and the amino acid composition of the protein (A) after electron beam irradiation were measured by the following method to identify an amino acid modified by the electron beam irradiation.

<Evaluation: Amino Acid Analysis>

Each protein (1 mg) was individually added to 6N hydrochloric acid (200 μL), followed by degassing. The solution was degassed until foam was no longer formed, and then the protein (A) in the solution was hydrolyzed under vacuum sealed conditions at 110° C. for 22 hours. After hydrolysis, the solution was diluted in deionized water to 800 μL. The diluted solution was filtered through a 0.45-μm filter to obtain a test sample. Table 3 shows the results.

Analysis was performed by LC-MSMS (Shimadzu Corporation) under the following conditions.

Column: InertSustain C18 (GL Sciences Inc.)

Mobile phase:
  A: 0.05 M aqueous solution of trifluoroacetic acid
  B: methanol
  A/B=95/5 (V/V)

Flow rate: 0.2 mL/min

Ion source: EST (+)

Measurement mode: MRM (MSMS)

The amino acid composition was determined from the elution time and the molecular weight of the standard sample (standard amino acid mixture: type H).

The amino acid in the protein (A) modified by the electron beam irradiation was serine.

Next, the compounds (HC) capable of forming a hydrogen bond with a hydroxyl group on the side chain of serine were screened with simulation software (Gaussian).

In addition, the compounds (HC) capable of forming a hydrogen bond with an amide group in the peptide bond of alanylalanine were screened.

As a result of screening, tryptophan, tyrosine, and histidine were identified as the hydrogen-bond-formable compounds (HC).

A hydroxyl group on the side chain of serine is considered to form a hydrogen bond (first hydrogen bond) with a carboxyl group on the side chain of tryptophan, a hydroxyl group on the side chain of tyrosine, or a carboxyl group on the side chain of histidine. Table 2 shows the distance (Å) of each first hydrogen bond.

An amide group in the peptide bond of alanylalanine is considered to form a hydrogen bond (second hydrogen bond) with a carboxyl group on the side chain of tryptophan, a hydroxyl group on the side chain of tyrosine, or a carboxyl group on the side chain of histidine. Table 2 shows the distance (Å) of each second hydrogen bond.

TABLE 2

| Hydrogen-bond-formable compound (HC) | Hydrogen bond distance (Å) Model compound | |
|---|---|---|
| | Serine | Alanyl alanine |
| Tryptophan | 1.778 | 1.774 |
| Tyrosine | 1.812 | 1.776 |
| Histidine | 1.802 | 1.823 |

Examples 1 to 32

Radiosterilization of Protein Compositions Each Containing SELP 8K

SELP 8K as the protein (A), the hydrogen-bond-formable compound (HC), the radical scavenger (RS), and water were mixed according to the weight ratio and the molar ratio described in Table 3 to obtain an aqueous solution of an unsterilized protein composition containing 2.4% by weight of SELP 8K for each example.

Subsequently, these unsterilized protein composition were freeze-dried and vacuum-packed in a nitrogen atmosphere. Each unsterilized protein had a water content of 8% by weight. The vacuum-packed unsterilized protein compositions were irradiated with electron beam at 25 kGy at −20° C. to produce protein compositions according to Examples 1 to 32.

Examples 33 to 65

Radiosterilization of Protein Compositions Each Containing ProNectin F

ProNectin F as the protein (A), the hydrogen-bond-formable compound (HC), the radical scavenger (RS), and water were mixed according to the weight ratio and the molar ratio described in Table 4 to obtain an aqueous solution of an unsterilized protein composition containing 2.4% by weight of ProNectin F for each example.

Subsequently, these unsterilized protein composition were freeze-dried and vacuum-packed in a nitrogen atmosphere. Each unsterilized protein had a water content of 5% by weight. The vacuum-packed unsterilized protein compositions were irradiated with electron beam at 25 kGy at −20° C. to produce protein compositions according to Examples 33 to 65.

Examples 66 to 97

Radiosterilization of Protein Compositions Each Containing ProNectin L

ProNectin L as the protein (A), the hydrogen-bond-formable compound (HC), the radical scavenger (RS), and water were mixed according to the weight ratio and the molar ratio described in Table 5 to obtain an aqueous solution of an unsterilized protein composition containing 2.4% by weight of ProNectin L for each example.

Subsequently, these unsterilized protein composition were freeze-dried and vacuum-packed in a nitrogen atmosphere. Each unsterilized protein had a water content of 4% by weight. The vacuum-packed unsterilized protein compositions were irradiated with electron beam at 25 kGy at −20° C. to produce protein compositions according to Examples 66 to 97.

Example 98

Radiosterilization of a Protein Composition Containing HRP-Conjugated Rabbit Antibody HRP-conjugated rabbit antibody as the protein (A), the hydrogen-bond-formable compound (HC), the radical scavenger (RS), and water were mixed according to the weight ratio and the molar ratio described in Table 6 to obtain an aqueous solution of an unsterilized protein composition containing 0.1% by weight of HRP-conjugated rabbit antibody.

Subsequently, the unsterilized protein composition was freeze-dried and vacuum-packed in a nitrogen atmosphere. The unsterilized protein had a water content of 7% by weight. The vacuum-packed unsterilized protein composition was irradiated with electron beam at 25 kGy at −20° C. to produce a protein composition according to Example 98.

Example 99

Radiosterilization of a Protein Composition Containing Glucose Oxidase

Glucose oxidase as the protein (A), the hydrogen-bond-formable compound (HC), the radical scavenger (RS), and water were mixed according to the weight ratio and the molar ratio described in Table 6 to obtain an aqueous solution of an unsterilized protein composition containing 2.4% by weight of glucose oxidase.

Subsequently, the unsterilized protein composition was freeze-dried and vacuum-packed in a nitrogen atmosphere. The unsterilized protein had a water content of 6% by weight. The vacuum-packed unsterilized protein composition was irradiated with electron beam at 25 kGy at −20° C. to produce a protein composition according to Example 99.

Example 100

Radiosterilization of a Protein Composition Containing Bovine Serum Albumin

Bovine serum albumin as the protein (A), the hydrogen-bond-formable compound (HC), the radical scavenger (RS), and water were mixed according to the weight ratio and the molar ratio described in Table 6 to obtain an aqueous solution of an unsterilized protein composition containing 2.4% by weight of bovine serum albumin.

Subsequently, the unsterilized protein composition was freeze-dried and vacuum-packed in a nitrogen atmosphere. The unsterilized protein had a water content of 5% by weight. The vacuum-packed unsterilized protein composition was irradiated with electron beam at 25 kGy at −20° C. to produce a protein composition according to Example 100.

Comparative Example 1

Radiosterilization of a Protein Composition Containing SELP 8K

SELP 8K as the protein (A) and water were mixed to obtain an aqueous solution of an unsterilized protein composition containing 2.4% by weight of SELP 8K.

Subsequently, the unsterilized protein composition was freeze-dried and vacuum-packed in a nitrogen atmosphere. The unsterilized protein had a water content of 8% by weight. The vacuum-packed unsterilized protein composition was irradiated with electron beam at 25 kGy at −20° C. to produce a protein composition according to Comparative Example 1.

Comparative Example 2

Radiosterilization of a Protein Composition Containing ProNectin F

ProNectin F as the protein (A) and water were mixed to obtain an aqueous solution of an unsterilized protein composition containing 2.4% by weight of ProNectin F.

Subsequently, the unsterilized protein composition was freeze-dried and vacuum-packed in a nitrogen atmosphere. The unsterilized protein had a water content of 5% by weight. The vacuum-packed unsterilized protein composition was irradiated with electron beam at 25 kGy at −20° C. to produce a protein composition according to Comparative Example 2.

Comparative Example 3

Radiosterilization of a Protein Composition Containing ProNectin L

ProNectin L as the protein (A) and water were mixed to obtain an aqueous solution of an unsterilized protein composition containing 2.4% by weight of ProNectin L.

Subsequently, the unsterilized protein composition was freeze-dried and vacuum-packed in a nitrogen atmosphere. The unsterilized protein had a water content of 4% by weight. The vacuum-packed unsterilized protein composition was irradiated with electron beam at 25 kGy at −20° C. to produce a protein composition according to Comparative Example 3.

Comparative Example 4

Radiosterilization of a Protein Composition Containing HRP-Conjugated Rabbit Antibody HRP-conjugated rabbit antibody as the protein (A) and water were mixed to obtain an aqueous solution of an unsterilized protein composition containing 0.1% by weight of HRP-conjugated rabbit antibody.

Subsequently, the unsterilized protein composition was freeze-dried and vacuum-packed in a nitrogen atmosphere. The unsterilized protein had a water content of 7% by weight. The vacuum-packed unsterilized protein composition was irradiated with electron beam at 25 kGy at −20° C. to produce a protein composition according to Comparative Example 4.

Comparative Example 5

Radiosterilization of a Protein Composition Containing Glucose Oxidase

Glucose oxidase as the protein (A) and water were mixed to obtain an aqueous solution of an unsterilized protein composition containing 2.4% by weight of glucose oxidase.

Subsequently, the unsterilized protein composition was freeze-dried and vacuum-packed in a nitrogen atmosphere. The unsterilized protein had a water content of 6% by weight. The vacuum-packed unsterilized protein composition was irradiated with electron beam at 25 kGy at −20° C. to produce a protein composition according to Comparative Example 5.

Comparative Example 6

Radiosterilization of a Protein Composition Containing Bovine Serum Albumin

Bovine serum albumin as the protein (A) and water were mixed to obtain an aqueous solution of an unsterilized protein composition containing 2.4% by weight of bovine serum albumin.

Subsequently, the unsterilized protein composition was freeze-dried and vacuum-packed in a nitrogen atmosphere. The unsterilized protein had a water content of 5% by weight. The vacuum-packed unsterilized protein composition was irradiated with electron beam at 25 kGy at −20° C. to produce a protein composition according to Comparative Example 6.

Comparative Example 7

Radiosterilization of a Protein Composition Containing SELP 8K

A protein composition according to Comparative Example 7 was produced as in Comparative Example 1, except that ascorbic acid as the radical scavenger was added in the proportion shown in Table 7.

Comparative Example 8

Radiosterilization of a Protein Composition Containing ProNectin F

A protein composition according to Comparative Example 8 was produced as in Comparative Example 2, except that ascorbic acid as the radical scavenger was added in the proportion shown in Table 7.

Comparative Example 9

Radiosterilization of a Protein Composition Containing ProNectin L

A protein composition according to Comparative Example 9 was produced as in Comparative Example 3, except that ascorbic acid as the radical scavenger was added in the proportion shown in Table 7.

Comparative Example 10

Radiosterilization of a Protein Composition Containing HRP-Conjugated Rabbit Antibody A protein composition according to Comparative Example 10 was produced as in Comparative Example 4, except that ascorbic acid as the radical scavenger was added in the proportion shown in Table 7.

Comparative Example 11

Radiosterilization of a Protein Composition Containing Glucose Oxidase

A protein composition according to Comparative Example 11 was produced as in Comparative Example 5, except that ascorbic acid as the radical scavenger was added in the proportion shown in Table 7.

Comparative Example 12

Radiosterilization of a Protein Composition Containing Bovine Serum Albumin

A protein composition according to Comparative Example 12 was produced as in Comparative Example 6, except that ascorbic acid as the radical scavenger was added in the proportion shown in Table 7.

Comparative Example 13

Radiosterilization of a Protein Composition Containing SELP 8K

A protein composition according to Comparative Example 13 was produced as in Comparative Example 1, except that ascorbic acid as the radical scavenger was added in the proportion shown in Table 7.

Comparative Example 14

Radiosterilization of a Protein Composition Containing ProNectin F

A protein composition according to Comparative Example 14 was produced as in Comparative Example 2, except that ascorbic acid as the radical scavenger was added in the proportion shown in Table 7.

Comparative Example 15

Radiosterilization of a Protein Composition Containing ProNectin L

A protein composition according to Comparative Example 15 was produced as in Comparative Example 3, except that ascorbic acid as the radical scavenger was added in the proportion shown in Table 7.

Comparative Example 16

Radiosterilization of a Protein Composition Containing SELP 8K

A protein composition according to Comparative Example 16 was produced as in Comparative Example 1, except that tryptophan as the hydrogen-bond-formable compound (HC) was added in the proportion shown in Table 7.

Comparative Example 17

Radiosterilization of a Protein Composition Containing ProNectin F

A protein composition according to Comparative Example 17 was produced as in Comparative Example 2, except that tryptophan as the hydrogen-bond-formable compound (HC) was added in the proportion shown in Table 7.

Comparative Example 18

Radiosterilization of a Protein Composition Containing ProNectin L

A protein composition according to Comparative Example 18 was produced as in Comparative Example 3, except that tryptophan as the hydrogen-bond-formable compound (HC) was added in the proportion shown in Table 7.

<Evaluation of the Denaturation Rate Calculated Based on HPLC Measurement>
(HPLC Measurement)

The unsterilized protein composition prepared for the production of the protein composition in each example and the protein composition according to each example were separately dissolved in deionized water (1 mL) to obtain solutions each containing 1 mg of the protein (A), and these solutions were filtered through a 0.45-μm filter to obtain test samples. Likewise, test samples of the unsterilized protein compositions prepared for the production of the protein compositions in the comparative examples and the protein compositions according to the comparative examples were prepared.

The test samples were measured by HPLC (Shimadzu Corporation) under the following conditions.
Column: Jupiter C4
Mobile phase:
  A: 99.85% by weight of water+0.15% by weight of trichloroacetic acid
  B: 34% by weight of acetonitrile+65.85% by weight of water+0.15% by weight of trichloroacetic acid
  C: 80% by weight of acetonitrile+19.85% by weight of water+0.15% by weight of trichloroacetic acid
Flow rate: 1 mL/min
Mode: curved gradient mode (A/B=86/14 to A/B=20/80 to C=100)
Measurement wavelength: 214 nm (Calculation of Denaturation Rate Calculated Based on HPLC Measurement)

The denaturation rate calculated based on HPLC measurement was determined from the following formula (1), wherein M is the peak height of the unsterilized protein composition and N is the peak height of the produced protein composition as measured under the above conditions. Tables 3 to 7 show the results.

$$\text{Denaturation rate (\%)} = \{1-(N/M)\} \times 100 \quad (1)$$

<Evaluation of the Denaturation Rate Calculated Based on LC-MSMS Measurement>
(Lc-Msms Measurement)

The unsterilized protein composition prepared for the production of the protein composition in each example and the protein composition according to each example were separately added to 6N hydrochloric acid (200 μL) to obtain solutions each containing 1 mg of the protein (A), followed by degassing. Each of these solutions was degassed until foam was no longer formed, and then the protein (A) in each solution was hydrolyzed under vacuum sealed conditions at 110° C. for 22 hours. After hydrolysis, each solution was diluted in deionized water to 800 μL. Each diluted solution was filtered through a 0.45-μm filter to obtain a test sample. Likewise, test samples of the unsterilized protein compositions prepared for the production of the protein compositions in the comparative examples and the protein compositions according to the comparative examples were prepared.

The test samples were analyzed by LC-MSMS (Shimadzu Corporation) under the following conditions.
Column: InertSustain C18 (GL Sciences Inc.)
Mobile phase:
  A: 0.05 M aqueous solution of trifluoroacetic acid
  B: methanol
  A/B=95/5 (V/V)
Flow rate: 0.2 mL/min
Ion source: ESI (+)
Measurement mode: MRM (MSMS)

The amino acid composition was determined from the elution time and the molecular weight of the standard sample (standard amino acid mixture: type H).

(Calculation of Denaturation Rate Calculated Based on LC-MSMS Measurement)

The denaturation rate calculated based on LC-MSMS measurement was determined from the following formula (2), wherein $O_n$ is the concentration of each amino acid in the unsterilized protein composition, $P_n$ is the concentration of each amino acid in the produced protein composition, and $Q$ is the number of types of amino acids measured, which were determined under the above conditions. Tables 3 to 7 show the results.

$$\text{Denaturation rate (\%)} = 1/Q \times \Sigma[1-(P_n/O_n)] \times 100 \quad (2)$$

TABLE 3

| | | Radical scavenger (RS) {Weight ratio [(RS)/A]} | | | | | | | Hydrogen-bond-formable compound (HC) {Molar ratio [(HC)/(A)]} | | | Denaturation rate (%) | |
|---|---|---|---|---|---|---|---|---|---|---|---|---|---|
| | Protein (A) | Ascorbic acid | Edaravone | Vanillin | Catechin | Gallic acid | Glutathione | Chlorogenic acid | Tryptophan | Tyrosine | Histidine | HPLC | LC-MSMS |
| Example 1 | SELP 8K | 0.01 | — | — | — | — | — | — | 0.01 | — | — | 1 | 3 |
| Example 2 | SELP 8K | 0.01 | — | — | — | — | — | — | 0.02 | — | — | 1 | 2 |

TABLE 3-continued

| | | Radical scavenger (RS) {Weight ratio [(RS)/A]} | | | | | | Hydrogen-bond-formable compound (HC) {Molar ratio [(HC)/(A)]} | | | Denaturation rate (%) | |
|---|---|---|---|---|---|---|---|---|---|---|---|---|---|
| | Protein (A) | As-corbic acid | Edara-vone | Va-nillin | Cate-chin | Gallic acid | Gluta-thione | Chloro-genic acid | Trypto-phan | Tyro-sine | Histi-dine | HPLC | LC-MSMS |
| Example 3 | SELP 8K | 0.01 | — | — | — | — | — | — | 0.05 | — | — | 1 | 2 |
| Example 4 | SELP 8K | 0.01 | — | — | — | — | — | — | 0.50 | — | — | 1 | 2 |
| Example 5 | SELP 8K | 0.01 | — | — | — | — | — | — | — | 0.01 | — | 12 | 4 |
| Example 6 | SELP 8K | 0.01 | — | — | — | — | — | — | — | 0.02 | — | 8 | 3 |
| Example 7 | SELP 8K | 0.01 | — | — | — | — | — | — | — | 0.05 | — | 7 | 3 |
| Example 8 | SELP 8K | 0.01 | — | — | — | — | — | — | — | 0.50 | — | 7 | 3 |
| Example 9 | SELP 8K | 0.01 | — | — | — | — | — | — | — | — | 0.01 | 10 | 8 |
| Example 10 | SELP 8K | 0.01 | — | — | — | — | — | — | — | — | 0.02 | 10 | 8 |
| Example 11 | SELP 8K | 0.01 | — | — | — | — | — | — | — | — | 0.05 | 9 | 4 |
| Example 12 | SELP 8K | 0.01 | — | — | — | — | — | — | — | — | 0.50 | 7 | 4 |
| Example 13 | SELP 8K | 0.10 | — | — | — | — | — | — | 0.02 | — | — | 1 | 2 |
| Example 14 | SELP 8K | 1.00 | — | — | — | — | — | — | 0.02 | — | — | 2 | 2 |
| Example 15 | SELP 8K | — | 0.01 | — | — | — | — | — | 0.02 | — | — | 2 | 5 |
| Example 16 | SELP 8K | — | 0.10 | — | — | — | — | — | 0.02 | — | — | 1 | 3 |
| Example 17 | SELP 8K | — | 1.00 | — | — | — | — | — | 0.02 | — | — | 1 | 3 |
| Example 18 | SELP 8K | — | — | 0.01 | — | — | — | — | 0.02 | — | — | 25 | 12 |
| Example 19 | SELP 8K | — | — | 0.10 | — | — | — | — | 0.02 | — | — | 16 | 10 |
| Example 20 | SELP 8K | — | — | 1.00 | — | — | — | — | 0.02 | — | — | 8 | 5 |
| Example 21 | SELP 8K | — | — | — | 0.01 | — | — | — | 0.02 | — | — | 5 | 8 |
| Example 22 | SELP 8K | — | — | — | 0.10 | — | — | — | 0.02 | — | — | 4 | 7 |
| Example 23 | SELP 8K | — | — | — | 1.00 | — | — | — | 0.02 | — | — | 4 | 7 |
| Example 24 | SELP 8K | — | — | — | — | 0.01 | — | — | 0.02 | — | — | 2 | 5 |
| Example 25 | SELP 8K | — | — | — | — | 0.10 | — | — | 0.02 | — | — | 2 | 5 |
| Example 26 | SELP 8K | — | — | — | — | 1.00 | — | — | 0.02 | — | — | 2 | 4 |
| Example 27 | SELP 8K | — | — | — | — | — | 0.01 | — | 0.02 | — | — | 2 | 2 |
| Example 28 | SELP 8K | — | — | — | — | — | 0.10 | — | 0.02 | — | — | 2 | 2 |
| Example 29 | SELP 8K | — | — | — | — | — | 1.00 | — | 0.02 | — | — | 2 | 1 |
| Example 30 | SELP 8K | — | — | — | — | — | — | 0.01 | 0.02 | — | — | 15 | 8 |
| Example 31 | SELP 8K | — | — | — | — | — | — | 0.10 | 0.02 | — | — | 9 | 6 |
| Example 32 | SELP 8K | — | — | — | — | — | — | 1.00 | 0.02 | — | — | 6 | 5 |

TABLE 4

| | Protein (A) | Radical scavenger (RS) {Weight ratio [(RS)/A]} | | | | | | | (Hydrogen-bond formable compound HC) {Molar ratio [(HC)/(A)]} | | | Denaturation rate (%) | |
|---|---|---|---|---|---|---|---|---|---|---|---|---|---|
| | | Ascorbic acid | Edaravone | Vanillin | Catechin | Gallic acid | Glutathione | Chlorogenic acid | Tryptophan | Tyrosine | Histidine | HPLC | LC-MSMS |
| Example 33 | Pro-Nectin F | 0.01 | — | — | — | — | — | — | 0.01 | — | — | 2 | 4 |
| Example 34 | Pro-Nectin F | 0.01 | — | — | — | — | — | — | 0.02 | — | — | 2 | 4 |
| Example 35 | Pro-Nectin F | 0.01 | — | — | — | — | — | — | 0.05 | — | — | 1 | 3 |
| Example 36 | Pro-Nectin F | 0.01 | — | — | — | — | — | — | 0.50 | — | — | 1 | 3 |
| Example 37 | Pro-Nectin F | 0.01 | — | — | — | — | — | — | — | 0.01 | — | 15 | 4 |
| Example 38 | Pro-Nectin F | 0.01 | — | — | — | — | — | — | — | 0.02 | — | 12 | 3 |
| Example 39 | Pro-Nectin F | 0.01 | — | — | — | — | — | — | — | 0.05 | — | 11 | 3 |
| Example 40 | Pro-Nectin F | 0.01 | — | — | — | — | — | — | — | 0.50 | — | 4 | 3 |
| Example 41 | Pro-Nectin F | 0.01 | — | — | — | — | — | — | — | — | 0.01 | 13 | 8 |
| Example 42 | Pro-Nectin F | 0.01 | — | — | — | — | — | — | — | — | 0.02 | 12 | 7 |
| Example 43 | Pro-Nectin F | 0.01 | — | — | — | — | — | — | — | — | 0.05 | 8 | 5 |
| Example 44 | Pro-Nectin F | 0.01 | — | — | — | — | — | — | — | — | 0.50 | 8 | 5 |
| Example 45 | Pro-Nectin F | 0.10 | — | — | — | — | — | — | 0.02 | — | — | 2 | 3 |
| Example 46 | Pro-Nectin F | 1.00 | — | — | — | — | — | — | 0.02 | — | — | 2 | 3 |
| Example 47 | Pro-Nectin F | — | 0.001 | — | — | — | — | — | 0.02 | — | — | 25 | 12 |
| Example 48 | Pro-Nectin F | — | 0.01 | — | — | — | — | — | 0.02 | — | — | 1 | 2 |
| Example 49 | Pro-Nectin F | — | 0.10 | — | — | — | — | — | 0.02 | — | — | 1 | 1 |
| Example 50 | Pro-Nectin F | — | 1.00 | — | — | — | — | — | 0.02 | — | — | 1 | 1 |
| Example 51 | Pro-Nectin F | — | — | 0.01 | — | — | — | — | 0.02 | — | — | 28 | 5 |
| Example 52 | Pro-Nectin F | — | — | 0.10 | — | — | — | — | 0.02 | — | — | 15 | 3 |
| Example 53 | Pro-Nectin F | — | — | 1.00 | — | — | — | — | 0.02 | — | — | 12 | 2 |
| Example 54 | Pro-Nectin F | — | — | — | 0.01 | — | — | — | 0.02 | — | — | 5 | 7 |
| Example 55 | Pro-Nectin F | — | — | — | 0.10 | — | — | — | 0.02 | — | — | 3 | 6 |
| Example 56 | Pro-Nectin F | — | — | — | 1.00 | — | — | — | 0.02 | — | — | 3 | 6 |
| Example 57 | Pro-Nectin F | — | — | — | — | 0.01 | — | — | 0.02 | — | — | 2 | 3 |
| Example 58 | Pro-Nectin F | — | — | — | — | 0.10 | — | — | 0.02 | — | — | 1 | 2 |
| Example 59 | Pro-Nectin F | — | — | — | — | 1.00 | — | — | 0.02 | — | — | 1 | 2 |
| Example 60 | Pro-Nectin F | — | — | — | — | — | 0.01 | — | 0.02 | — | — | 21 | 4 |
| Example 61 | Pro-Nectin F | — | — | — | — | — | 0.10 | — | 0.02 | — | — | 14 | 3 |
| Example 62 | Pro-Nectin F | — | — | — | — | — | 1.00 | — | 0.02 | — | — | 11 | 3 |
| Example 63 | Pro-Nectin F | — | — | — | — | — | — | 0.01 | 0.02 | — | — | 18 | 4 |
| Example 64 | Pro-Nectin F | — | — | — | — | — | — | 0.10 | 0.02 | — | — | 12 | 3 |
| Example 65 | Pro-Nectin F | — | — | — | — | — | — | 1.00 | 0.02 | — | — | 11 | 3 |

TABLE 5

| | Protein (A) | Radical scavenger (RS) [Weight ratio [(RS)/A]] | | | | | | | Hydrogen-bond formable compound (HC) [Molar ratio [(HC)/(A)]] | | | Denaturation rate (%) | |
|---|---|---|---|---|---|---|---|---|---|---|---|---|---|
| | | Ascorbic acid | Edaravone | Vanillin | Catechin | Gallic acid | Gluta-thione | Chlorogenic acid | Tryptophan | Tyrosine | Histidine | HPLC | LC-MSMS |
| Example 66 | Pro-Nectin L | 0.01 | — | — | — | — | — | — | 0.01 | — | — | 1 | 6 |
| Example 67 | Pro-Nectin L | 0.01 | — | — | — | — | — | — | 0.02 | — | — | 1 | 5 |
| Example 68 | Pro-Nectin L | 0.01 | — | — | — | — | — | — | 0.05 | — | — | 1 | 5 |
| Example 69 | Pro-Nectin L | 0.01 | — | — | — | — | — | — | 0.50 | — | — | 1 | 5 |
| Example 70 | Pro-Nectin L | 0.01 | — | — | — | — | — | — | — | 0.01 | — | 20 | 5 |
| Example 71 | Pro-Nectin L | 0.01 | — | — | — | — | — | — | — | 0.02 | — | 19 | 4 |
| Example 72 | Pro-Nectin L | 0.01 | — | — | — | — | — | — | — | 0.05 | — | 15 | 4 |
| Example 73 | Pro-Nectin L | 0.01 | — | — | — | — | — | — | — | 0.50 | — | 11 | 5 |
| Example 74 | Pro-Nectin L | 0.01 | — | — | — | — | — | — | — | — | 0.01 | 18 | 9 |
| Example 75 | Pro-Nectin L | 0.01 | — | — | — | — | — | — | — | — | 0.02 | 17 | 6 |
| Example 76 | Pro-Nectin L | 0.01 | — | — | — | — | — | — | — | — | 0.05 | 12 | 5 |
| Example 77 | Pro-Nectin L | 0.01 | — | — | — | — | — | — | — | — | 0.50 | 10 | 5 |
| Example 78 | Pro-Nectin L | 0.10 | — | — | — | — | — | — | 0.02 | — | — | 1 | 5 |
| Example 79 | Pro-Nectin L | 1.00 | — | — | — | — | — | — | 0.02 | — | — | 1 | 5 |
| Example 80 | Pro-Nectin L | — | 0.01 | — | — | — | — | — | 0.02 | — | — | 1 | 4 |
| Example 81 | Pro-Nectin L | — | 0.10 | — | — | — | — | — | 0.02 | — | — | 1 | 4 |
| Example 82 | Pro-Nectin L | — | 1.00 | — | — | — | — | — | 0.02 | — | — | 1 | 3 |
| Example 83 | Pro-Nectin L | — | — | 0.01 | — | — | — | — | 0.02 | — | — | 26 | 5 |
| Example 84 | Pro-Nectin L | — | — | 0.10 | — | — | — | — | 0.02 | — | — | 11 | 3 |
| Example 85 | Pro-Nectin L | — | — | 1.00 | — | — | — | — | 0.02 | — | — | 10 | 3 |
| Example 86 | Pro-Nectin L | — | — | — | 0.01 | — | — | — | 0.02 | — | — | 2 | 7 |
| Example 87 | Pro-Nectin L | — | — | — | 0.10 | — | — | — | 0.02 | — | — | 2 | 7 |
| Example 88 | Pro-Nectin L | — | — | — | 1.00 | — | — | — | 0.02 | — | — | 2 | 5 |
| Example 89 | Pro-Nectin L | — | — | — | — | 0.01 | — | — | 0.02 | — | — | 1 | 5 |
| Example 90 | Pro-Nectin L | — | — | — | — | 0.10 | — | — | 0.02 | — | — | 1 | 5 |
| Example 91 | Pro-Nectin L | — | — | — | — | 1.00 | — | — | 0.02 | — | — | 1 | 4 |
| Example 92 | Pro-Nectin L | — | — | — | — | — | 0.01 | — | 0.02 | — | — | 10 | 6 |
| Example 93 | Pro-Nectin L | — | — | — | — | — | 0.10 | — | 0.02 | — | — | 7 | 5 |
| Example 94 | Pro-Nectin L | — | — | — | — | — | 1.00 | — | 0.02 | — | — | 7 | 5 |
| Example 95 | Pro-Nectin L | — | — | — | — | — | — | 0.01 | 0.02 | — | — | 7 | 5 |
| Example 96 | Pro-Nectin L | — | — | — | — | — | — | 0.10 | 0.02 | — | — | 6 | 5 |
| Example 97 | Pro-Nectin L | — | — | — | — | — | — | 1.00 | 0.02 | — | — | 5 | 4 |

TABLE 6

| | | Radical scavenger (RS) {Weight ratio [(RS)/A]} | | | | | | | Hydrogen-bond-formable compound (HC) {Molar ratio [(HC)/(A)]} | | | Denaturation rate (%) | |
|---|---|---|---|---|---|---|---|---|---|---|---|---|---|
| | Protein (A) | Ascorbic acid | Edaravone | Vanillin | Catechin | Gallic acid | Glutathione | Chlorogenic acid | Tryptophan | Tyrosine | Histidine | HPLC | LC-MSMS |
| Example 98 | HRP-conjugated rabbit antibody | 0.01 | — | — | — | — | — | — | 0.02 | — | — | 22 | 5 |
| Example 99 | Glucose oxidase | 0.01 | — | — | — | — | — | — | 0.02 | — | — | 12 | 5 |
| Example 100 | Bovine serum albumin | 0.01 | — | — | — | — | — | — | 0.02 | — | — | 7 | 4 |

TABLE 7

| | | Radical scavenger (RS) {Weight ratio [(RS)/A]} | | | | | | | Hydrogen-bond-formable compound (HC) {Molar ratio [(HC)/(A)]} | | | Denaturation rate (%) | |
|---|---|---|---|---|---|---|---|---|---|---|---|---|---|
| | Protein (A) | Ascorbic acid | Edaravone | Vanillin | Catechin | Gallic acid | Glutathione | Chlorogenic acid | Tryptophan | Tyrosine | Histidine | HPLC | LC-MSMS |
| Comparative Example 1 | SELP 8K | — | — | — | — | — | — | — | — | — | — | 30 | 15 |
| Comparative Example 2 | Pro-Nectin F | — | — | — | — | — | — | — | — | — | — | 50 | 10 |
| Comparative Example 3 | Pro-Nectin L | — | — | — | — | — | — | — | — | — | — | 45 | 12 |
| Comparative Example 4 | HRP-conjugated rabbit antibody | — | — | — | — | — | — | — | — | — | — | 85 | 22 |
| Comparative Example 5 | Glucose oxidase | — | — | — | — | — | — | — | — | — | — | 70 | 18 |
| Comparative Example 6 | Bovine serum albumin | — | — | — | — | — | — | — | — | — | — | 62 | 10 |
| Comparative Example 7 | SELP 8K | 0.01 | — | — | — | — | — | — | — | — | — | 29 | 15 |
| Comparative Example 8 | Pro-Nectin F | 0.01 | — | — | — | — | — | — | — | — | — | 48 | 11 |
| Comparative Example 9 | Pro-Nectin L | 0.01 | — | — | — | — | — | — | — | — | — | 42 | 10 |
| Comparative Example 10 | HRP-conjugated rabbit antibody | 0.01 | — | — | — | — | — | — | — | — | — | 83 | 19 |
| Comparative Example 11 | Glucose oxidase | 0.01 | — | — | — | — | — | — | — | — | — | 66 | 18 |
| Comparative Example 12 | Bovine serum albumin | 0.01 | — | — | — | — | — | — | — | — | — | 60 | 10 |
| Comparative Example 13 | SELP 8K | 0.001 | — | — | — | — | — | — | — | — | — | 28 | 12 |
| Comparative Example 14 | Pro-Nectin F | 0.001 | — | — | — | — | — | — | — | — | — | 49 | 11 |
| Comparative Example 15 | Pro-Nectin L | 0.001 | — | — | — | — | — | — | — | — | — | 42 | 10 |
| Comparative Example 16 | SELP 8K | — | — | — | — | — | — | — | 0.005 | — | — | 28 | 12 |
| Comparative Example 17 | Pro-Nectin F | — | — | — | — | — | — | — | 0.005 | — | — | 49 | 16 |
| Comparative Example 18 | Pro-Nectin L | — | — | — | — | — | — | — | 0.005 | — | — | 44 | 12 |

The results in Tables 3 to 7 show that the denaturation rate of the protein (A) is lower in each of the protein compositions obtained by the production method of the present invention than that in the protein compositions according to Comparative Examples 1 to 18.

INDUSTRIAL APPLICABILITY

The method for producing a protein composition of the present invention is excellent in allowing a protein composition to maintain physiological and physicochemical functions of a protein when the protein composition is subjected to radiosterilization. Thus, the present invention is effective as a method for producing a protein composition.

---

The invention claimed is:

1. A method for producing a protein composition containing a protein (A), a radical scavenger (RS), and at least one hydrogen-bond-formable compound (HC) selected from the group consisting of amino acids, peptides, and proteins other than the protein (A), the method comprising:
a sterilization step of radiosterilizing a freeze-dried and unsterilized protein composition,
wherein the unsterilized protein composition contains the protein (A), the radical scavenger (RS), and the hydrogen-bond-formable compound (HC), the protein (A) contains at least one functional group selected from the group consisting of sulfide, amide, hydroxyl, amino, and carboxyl groups, the hydrogen-bond-formable compound (HC) contains at least one functional group selected from the group consisting of sulfide, amide, hydroxyl, amino, and carboxyl groups, the at least one functional group in the protein (A) is capable of binding to the at least one functional group in the hydrogen-bond-formable compound (HC) via a hydrogen bond, the unsterilized protein composition has a water content of 0 to 30% by weight based on the weight of the unsterilized protein composition, a weight ratio of the radical scavenger (RS) to the protein (A) in the unsterilized protein composition is 0.01 to 1.0, a molar ratio of a total molar number of functional groups in the hydrogen-bond-formable compound (HC) to a total molar number of functional groups in the protein (A) in the unsterilized protein composition is 0.05 to 0.50, the method further comprises a freeze-drying step performed before the sterilization step, in the freeze-drying step, a water solution containing the protein (A), the radical scavenger (RS), and the hydrogen-bond-formable compound (HC) is freeze-dried to the unsterilized protein composition, and the protein (A) is SELP 8K containing an amino acid sequence represented by SEQ ID NO: 22.

2. The method for producing a protein composition according to claim 1, wherein in the unsterilized protein composition, the at least one functional group of the protein (A) is on a side chain of an amino acid, the at least one functional group on a side chain of an amino acid in the protein (A) is capable of binding to the at least one functional group in the hydrogen-bond-formable compound (HC) via a first hydrogen bond, the first hydrogen bond has a distance of 1.3 to 1.9 Å, and the distance of the first hydrogen bond is a distance between a donor hydrogen and an acceptor.

3. The method for producing a protein composition according to claim 1, wherein in the unsterilized protein composition, the at least one functional group in the protein (A) is an amide group in a peptide bond in the protein (A), the amide group in a peptide bond in the protein (A) is bound to the hydrogen-bond-formable compound (HC) via a second hydrogen bond, and the second hydrogen bond has a distance of 1.3 to 1.9 Å, and the distance of the first hydrogen bond is a distance between a donor hydrogen and an acceptor.

4. The method for producing a protein composition according to claim 1, wherein the protein (A) has a molecular mass of 15 to 200 kDa as determined by SDS-polyacrylamide gel electrophoresis.

5. The method for producing a protein composition according to claim 1, wherein the radical scavenger (RS) has a structure that is at least one selected from the group consisting of oxygen-containing conjugated structures and nitrogen-containing conjugated structures.

6. The method for producing a protein composition according to claim 1, wherein the radical scavenger (RS) has a radical scavenging ability against diphenylpicrylhydrazyl radicals of 0.01 to 90 mg Trolox eq/mg.

* * * * *